United States Patent
Kwon et al.

(10) Patent No.: US 12,065,394 B2
(45) Date of Patent: Aug. 20, 2024

(54) COMPOUND AND PHARMACEUTICAL COMPOSITION FOR PREVENTING OR TREATING OBESITY OR METABOLIC SYNDROME COMPRISING THEREOF

(71) Applicant: Seoul National University R&DB Foundation, Seoul (KR)

(72) Inventors: Yong Tae Kwon, Seoul (KR); Srinivasrao Ganipisetti, Seoul (KR); Ki Woon Sung, Seoul (KR); Eui Jung Jung, Seoul (KR); Tae Hyun Bae, Seoul (KR); Su Ran Mun, Seoul (KR); Chan Hoon Jung, Seoul (KR)

(73) Assignee: Seoul National University R&DBFoundation, Seoul (KR)

( * ) Notice: Subject to any disclaimer, the term of this patent is extended or adjusted under 35 U.S.C. 154(b) by 918 days.

(21) Appl. No.: 17/041,960

(22) PCT Filed: Mar. 26, 2019

(86) PCT No.: PCT/KR2019/003514
§ 371 (c)(1),
(2) Date: Sep. 25, 2020

(87) PCT Pub. No.: WO2019/190172
PCT Pub. Date: Oct. 3, 2019

(65) Prior Publication Data
US 2021/0024454 A1    Jan. 28, 2021

Related U.S. Application Data

(60) Provisional application No. 62/648,381, filed on Mar. 26, 2018.

(51) Int. Cl.
*C07C 215/50* (2006.01)
*A61P 3/04* (2006.01)

(52) U.S. Cl.
CPC .............. *C07C 215/50* (2013.01); *A61P 3/04* (2018.01)

(58) Field of Classification Search
CPC .................................. C07C 215/50; A61P 3/04
See application file for complete search history.

(56) References Cited

U.S. PATENT DOCUMENTS

| 5,495,046 A | 2/1996 | Nakazato et al. |
| 5,576,340 A | 11/1996 | Fujita et al. |
| 2002/0120011 A1 | 8/2002 | Sikorski et al. |
| 2015/0175607 A1 | 6/2015 | Xie et al. |
| 2018/0243244 A1 | 8/2018 | Kwon et al. |

FOREIGN PATENT DOCUMENTS

| CN | 103930166 A | 7/2014 | |
| JP | 1994329535 A | 11/1994 | |
| JP | 2768008 B2 | 9/1998 | |
| KR | 20090035707 A | 4/2009 | |
| KR | 20150039894 A | 4/2015 | |
| KR | 1020170021525 A | 5/2017 | |
| WO | 2013022919 A1 | 2/2013 | |
| WO | 2016200827 A1 | 2/2013 | |
| WO | WO-2013022919 A1 * | 2/2013 | ........... A61K 31/137 |
| WO | 2017030292 A1 | 2/2017 | |

OTHER PUBLICATIONS

English abstract of WO2017030292; retrieved from www.espacenet.com on Nov. 12, 2021.
International Search Report and Written Opinion of PCT/KR2019/003514, mailed Jun. 24, 2019.
Translation of International Search Report of PCT/KR2019/003514, mailed Jun. 24, 2019.
English abstract of KR20090035707.
English abstract of KR1020170021525.
English Abstract of KR1020150039894.
English Abstract of JP2768008.
English Abstract of JP1994329535.
Anding AL, Baehrecke EH, "Cleaning House, Selective Autophagy of Organelles", Developmental cell 2017, 10, 41, 10-22.
Centers of Disease Control and Prevention, Adult Obesity Facts, https://www.cdc.gov/odesity/data/adult.html.
Cummings DE, and Schwartz MW., "Genetics and Pathophysiology of Human Obesity", Annu Rev Med (2003) 54 453-47.
Daneschvar HI, Smetana GW., MDFDA—Approved Anti-Obesity Drugs in the United States., The Am J Med 2016, 129, 879, e1-879.e6.
Dobbs R. et al., Overcoming Obesity an Initial Economic Analysis, Mckinesey Global Institute, 2014.
Global, regional and national prevalence of overweight and obesity in children and adults 1980-2013 A systematic analysis, Lancet. Aug. 30, 2014; 384(9945): 766-781.
Identification and Characterization of Inhibitors of the Aminoglycoside, ChemMedChem 2012, 1, 73-77.
Jean-Rene Pallandre et al., Novel aminotetrazole derivatives as selective STAT3 non-peptide inhibitors, European Journal of Medicinal Chemistry, 103 (2015) 163-174.

(Continued)

*Primary Examiner* — Matthew P Coughlin
*Assistant Examiner* — Meghan C Heasley
(74) *Attorney, Agent, or Firm* — Polsinelli PC

(57) ABSTRACT

The present invention provides a compound represented by the following Chemical Formula 1 or a pharmaceutically acceptable salt thereof which can be effectively used for preventing or treating obesity or metabolic syndrome, and a pharmaceutical composition comprising the same.

[Chemical Formula 1]

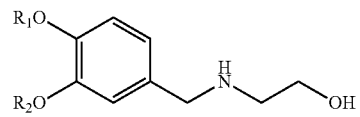

in Chemical Formula 1,
$R_1$ and $R_2$ are the same as defined in the specification.

9 Claims, 13 Drawing Sheets

(56) References Cited

OTHER PUBLICATIONS

Kaushik S, Cuervo AM, Degradation of lipid droplet-associated proteins by chaperone-mediated autophagy facilitates lipolysis, Nat Cell Biol. Jun. 2015 ; 17(6): 759-770. doi:10.1038/ncb3166.

Kneeman JM, Misdraji J, Corey KE. Secondary causes of nonalcoholic fatty liver disease, Therapeutic Advances in Gastroenterology, 2012.

World Health Organization, Regional for Europe. Obesity internet. Geneva, World Health Oraganization, c2013(cited Mar. 30, 2013).

English abstract of CN 103930166A, 1 page.

Extended European Search Report issued for application No. 19774785.0, issued on Jan. 1, 31, 2022, 5 pages.

* cited by examiner

[Fig.1]
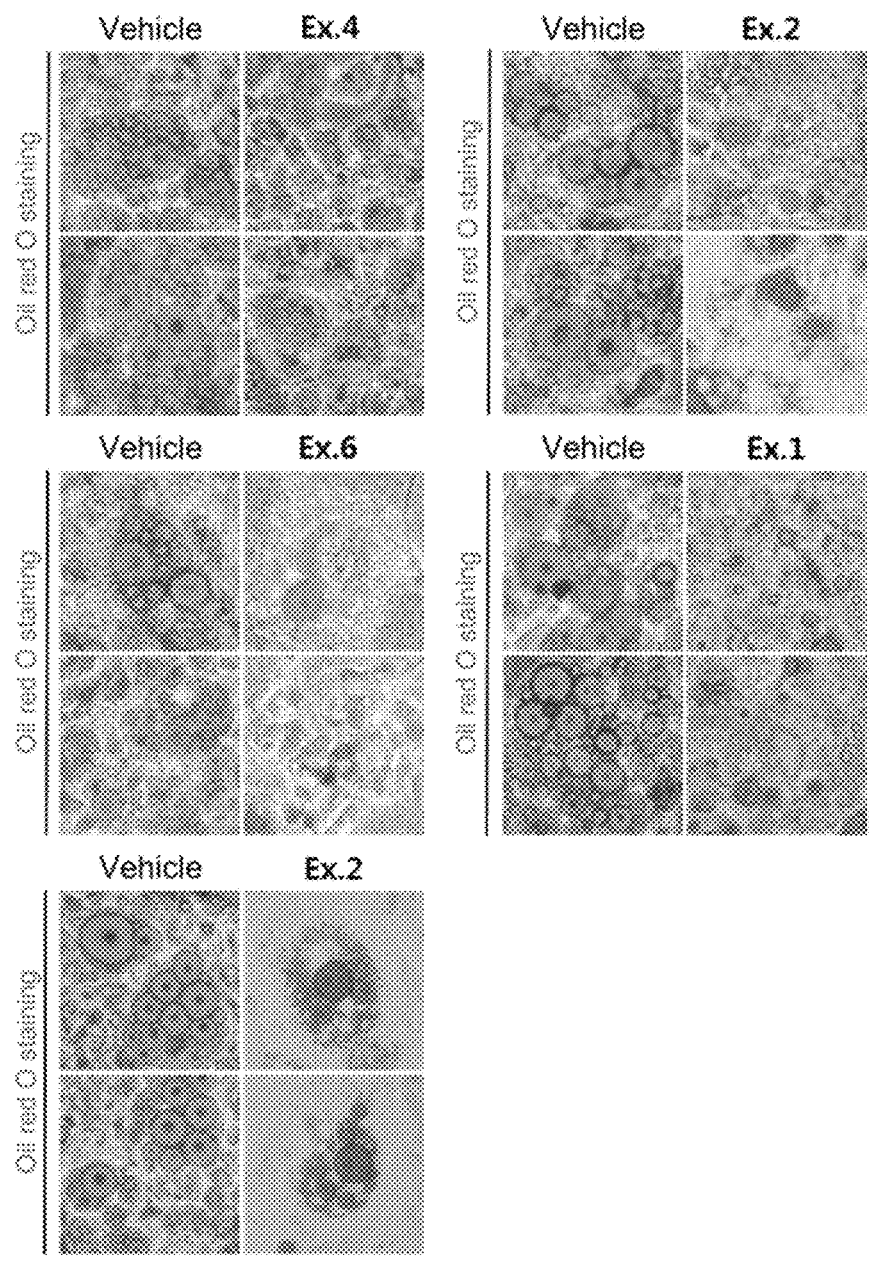
3T3L1, adipocyte

[Fig.2]
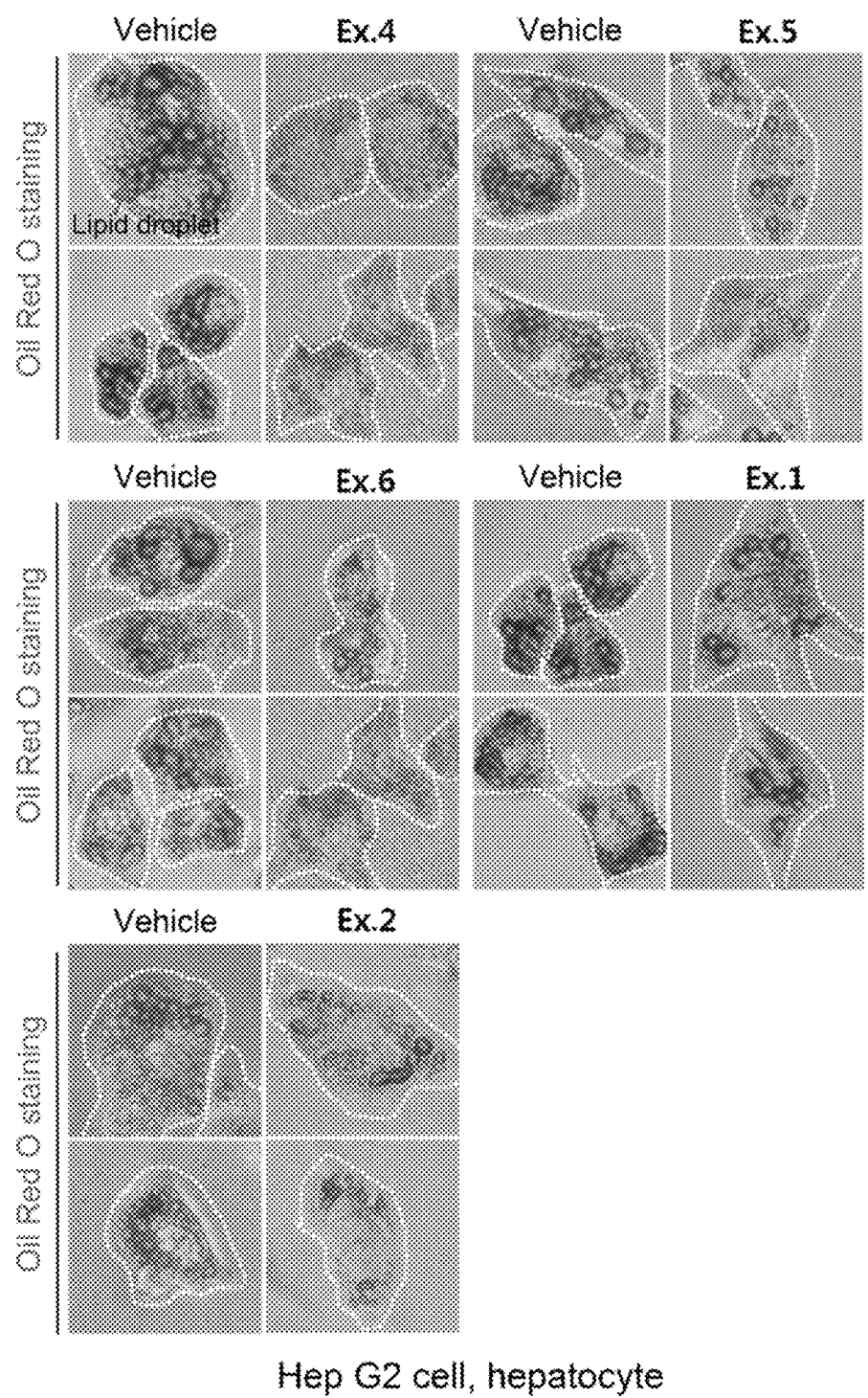
Hep G2 cell, hepatocyte

[Fig. 3]
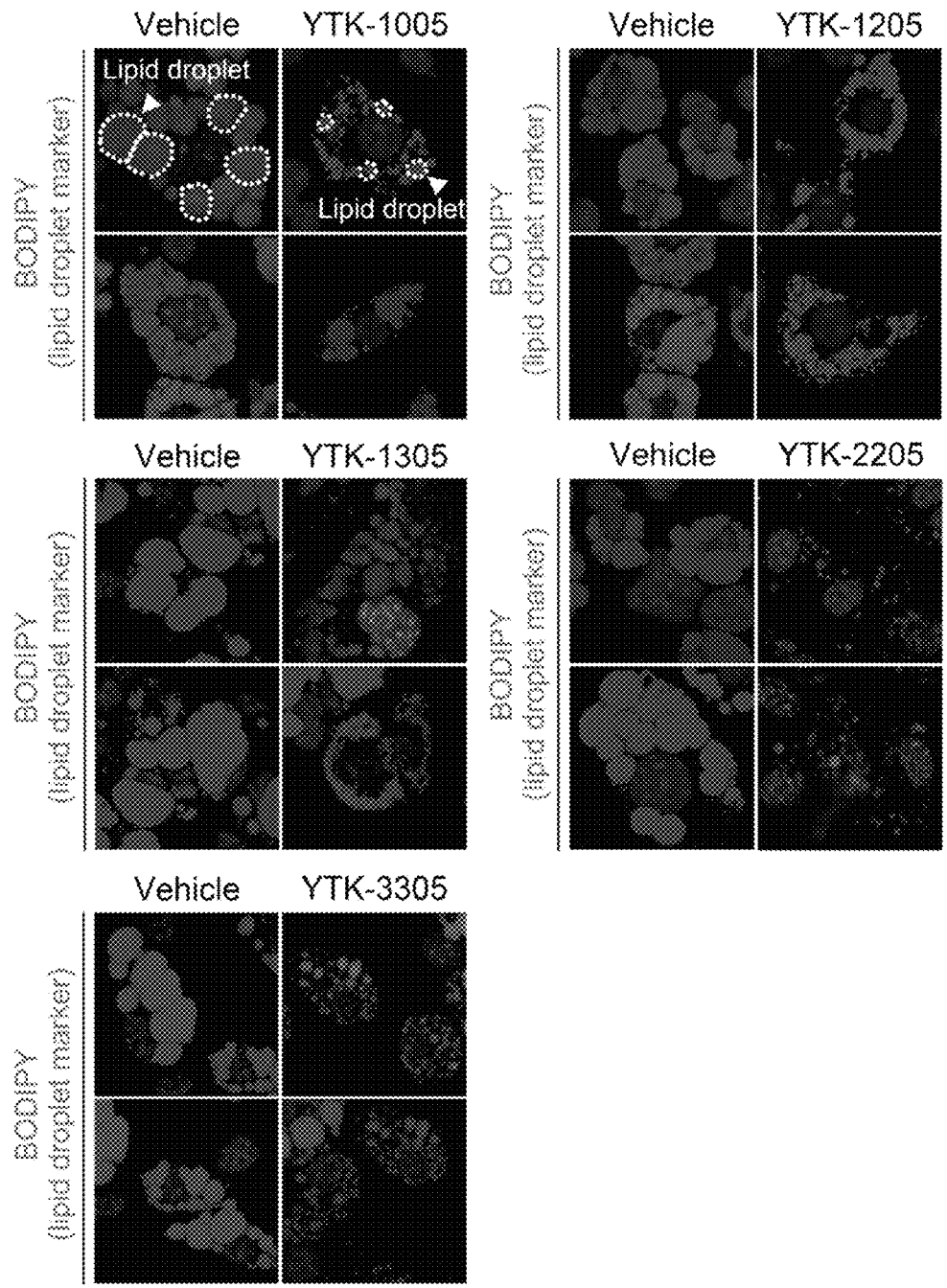
3T3L1, adipocyte

[Fig. 4a]
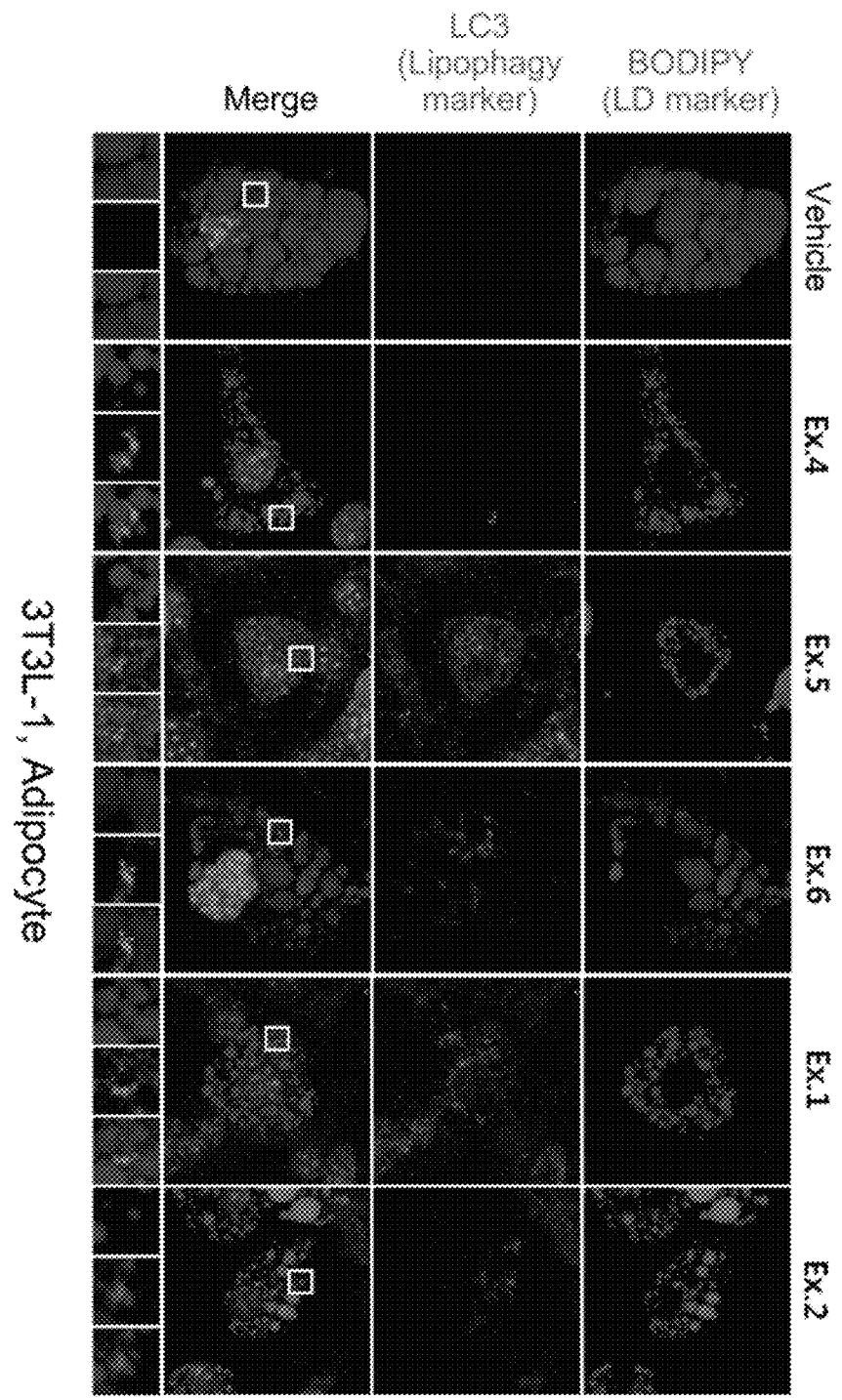

[Fig. 4b]
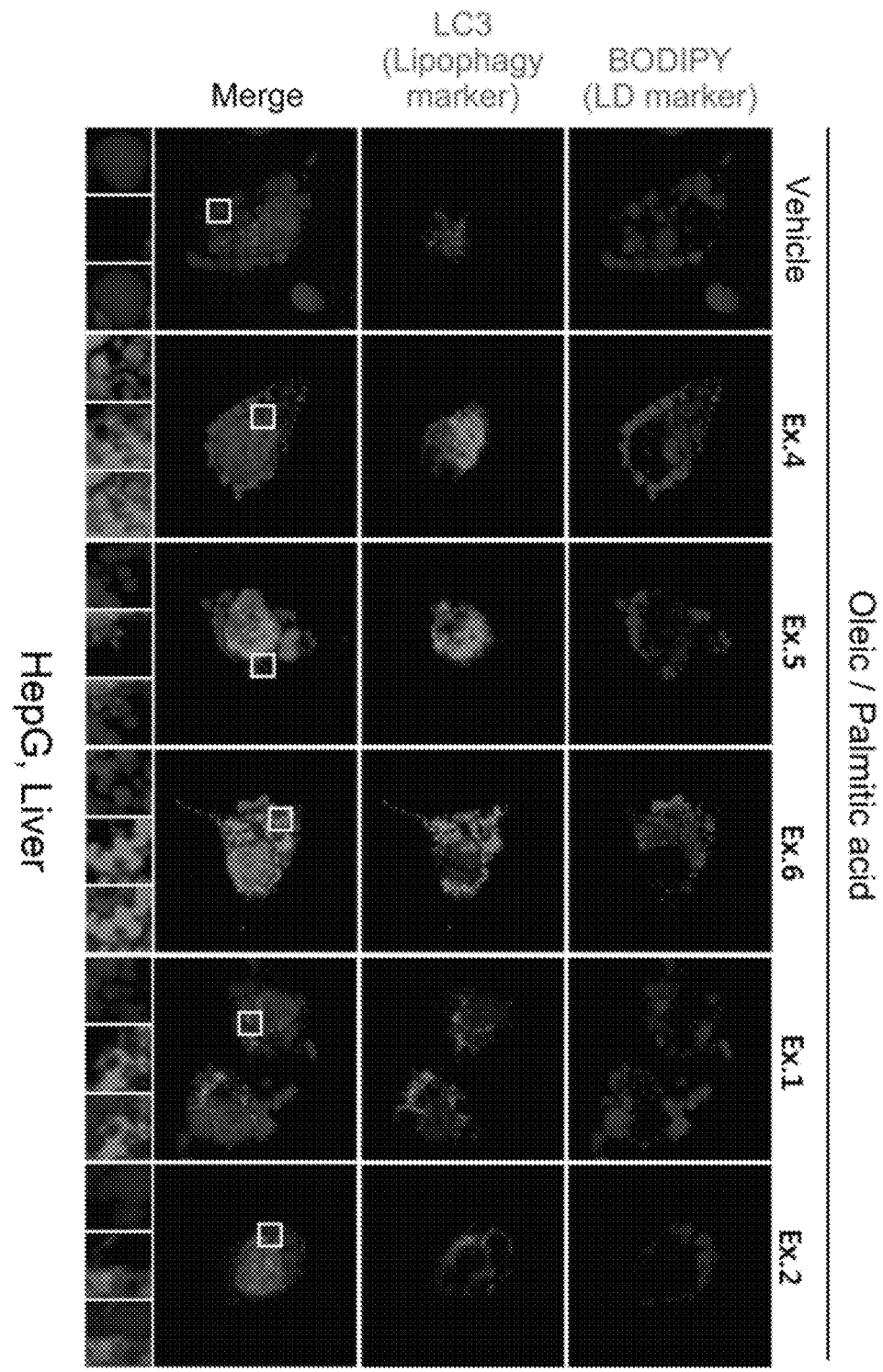

[Fig. 5]
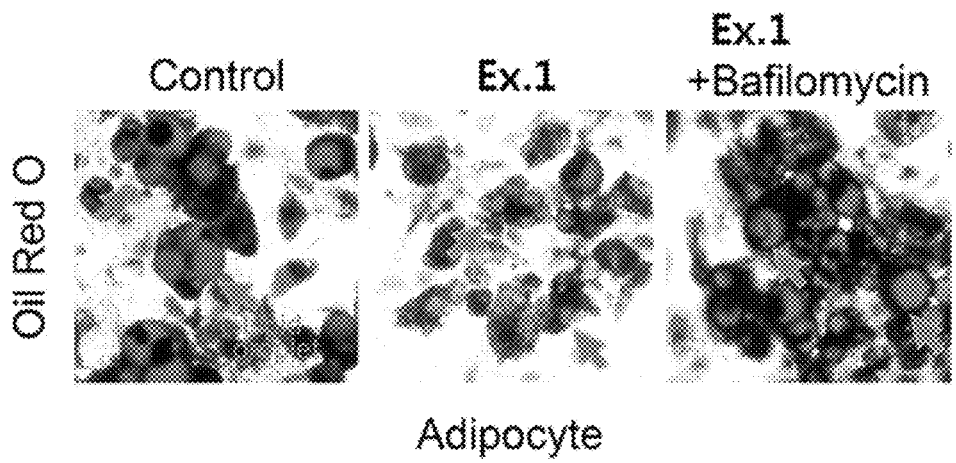
[Fig. 6]
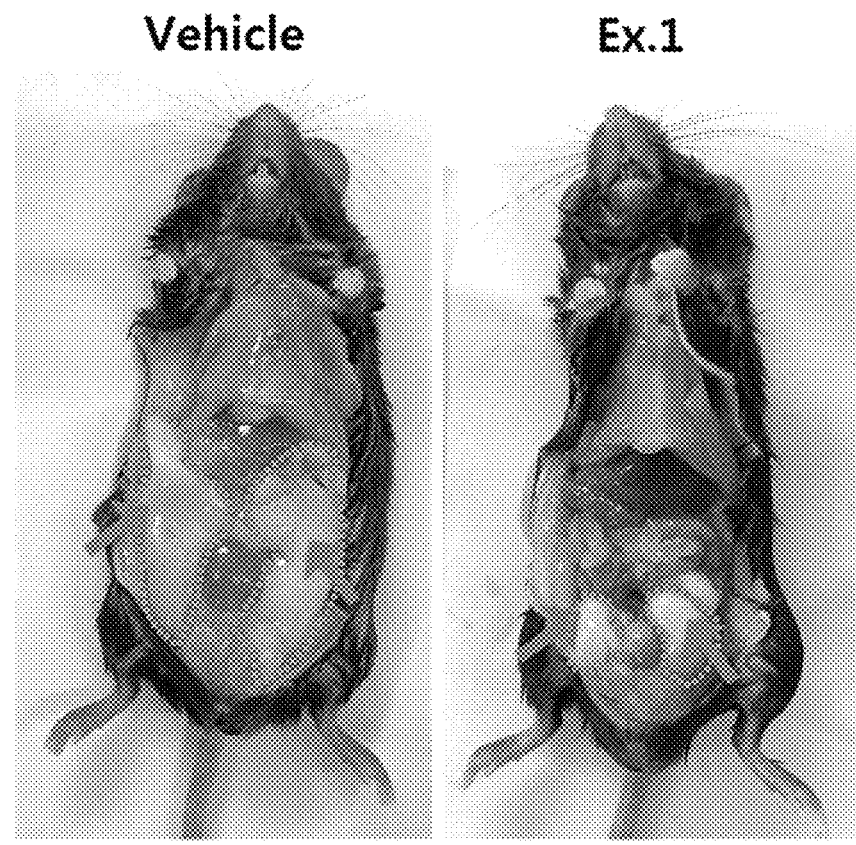

[Fig. 7]
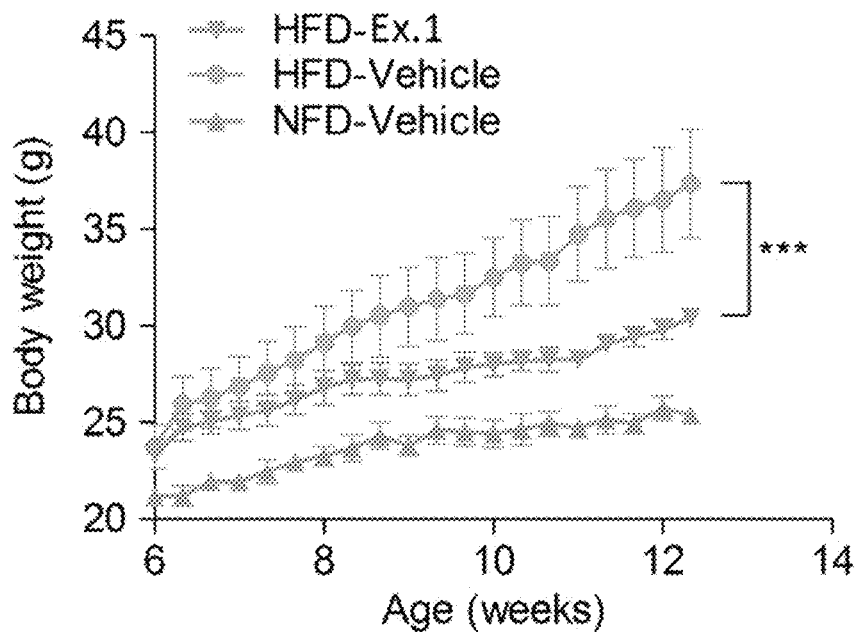
[Fig. 8]
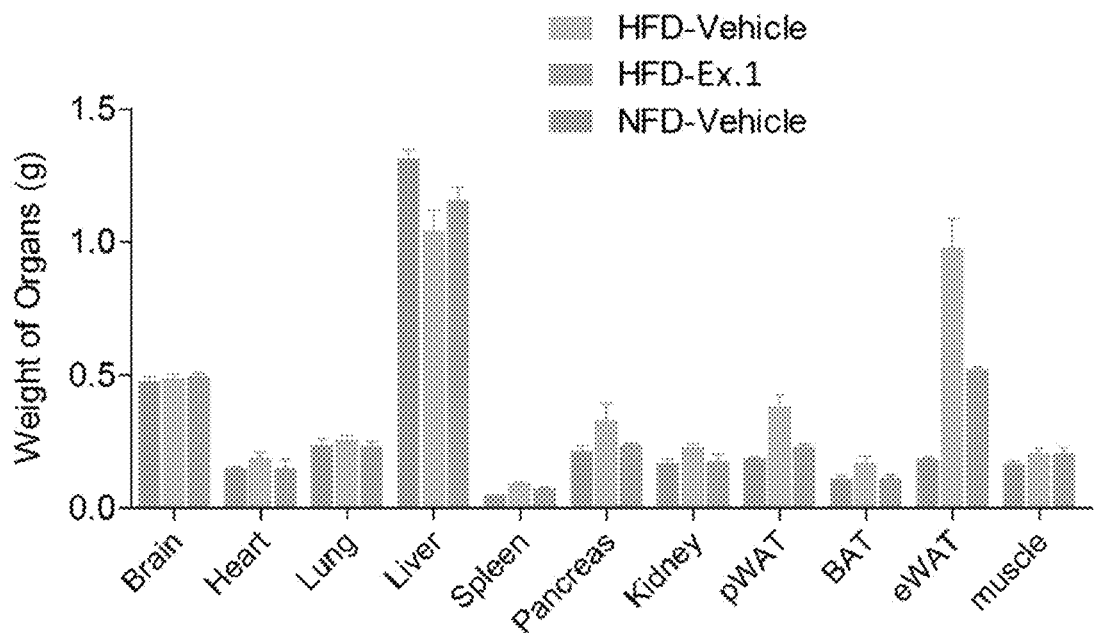

[Fig. 9]
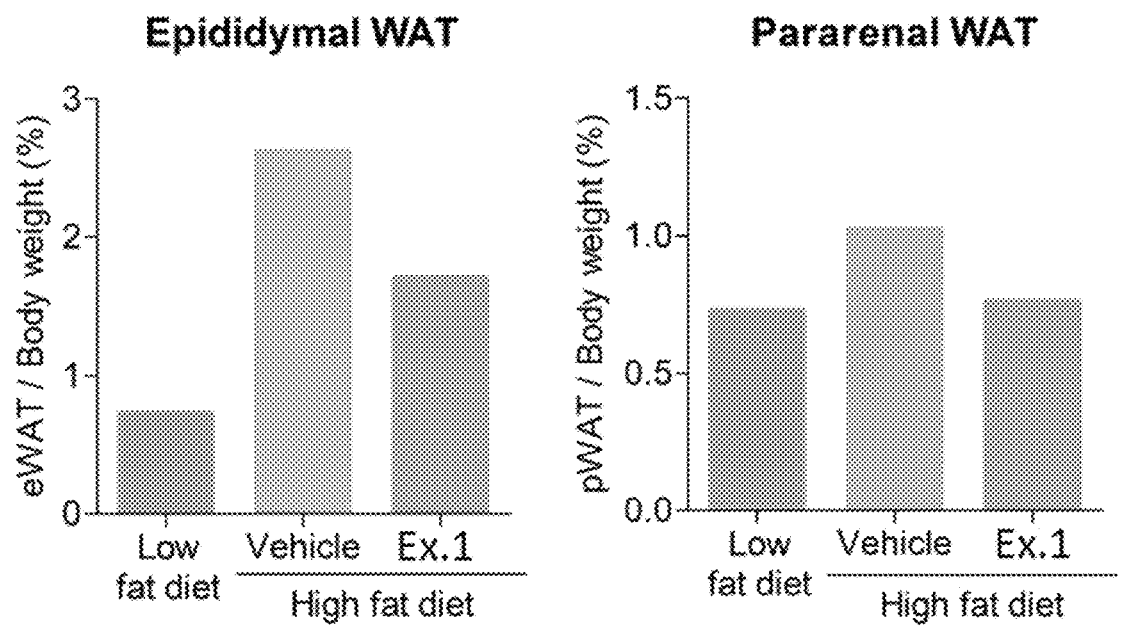
[Fig. 10]
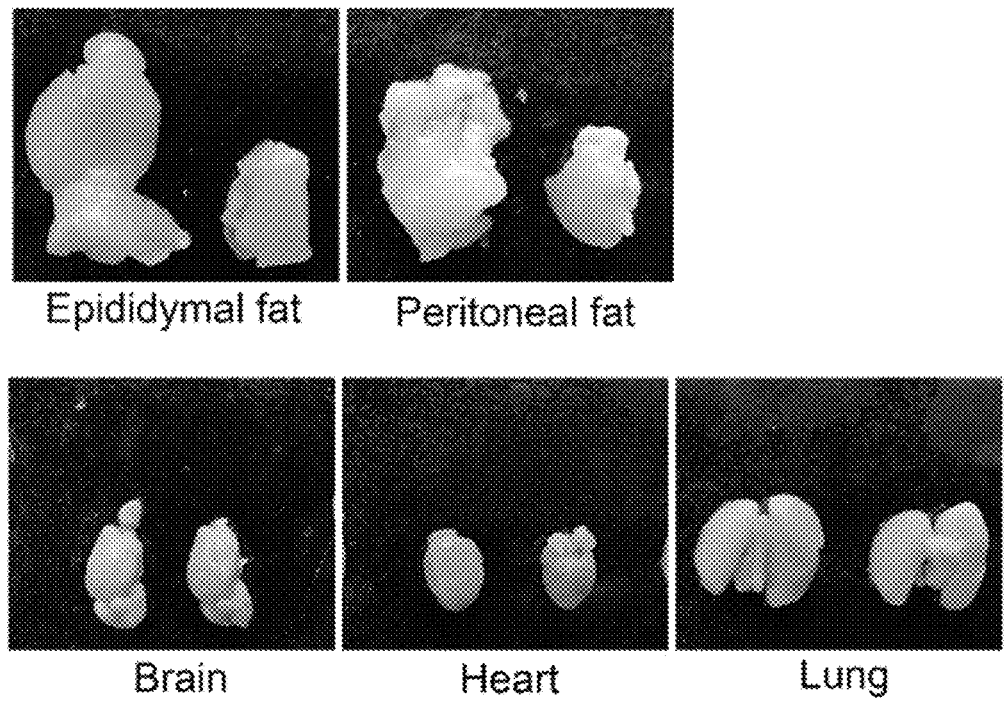

[Fig. 11]
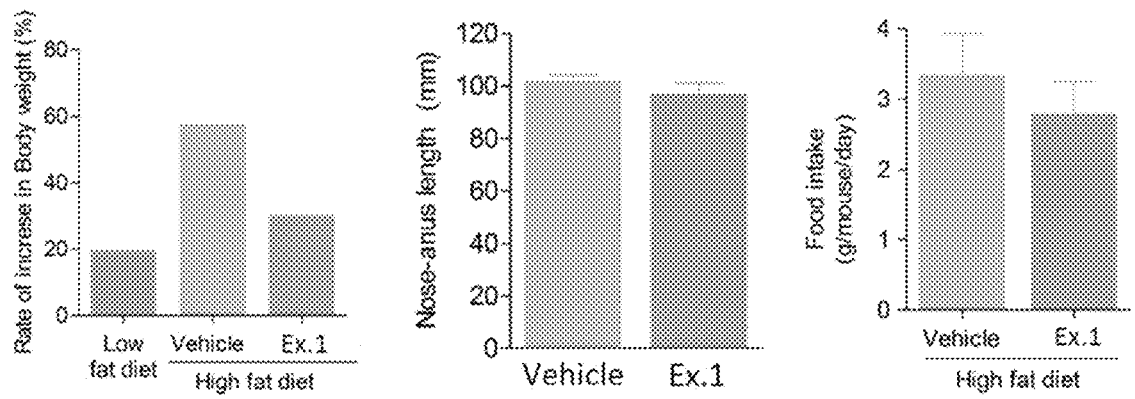
[Fig. 12]
|  | Vehicle | Ex.1 |
| --- | --- | --- |
| Inorganic phosphorus (2.5-4.5 mg/dl) | 8.57 | 8.37 |
| Blood urea nitrogen (7-20 mg/dl) | 24.33 | 29.87 |
| Uric acid (0.5-1.5 mg/dl) | 2.00 | 2.00 |
| Total protein (6.4-8.0 g/dl) | 4.77 | 4.77 |
| Albumin (3.5-4.5 g/dl) | 1.80 | 1.80 |
| Glucose (70-100 mg/dl) | 151.33 | 142.00 |
| Triglyceride (3.89 mmol/L) | 17.67 | 14.00 |

[Fig. 13]
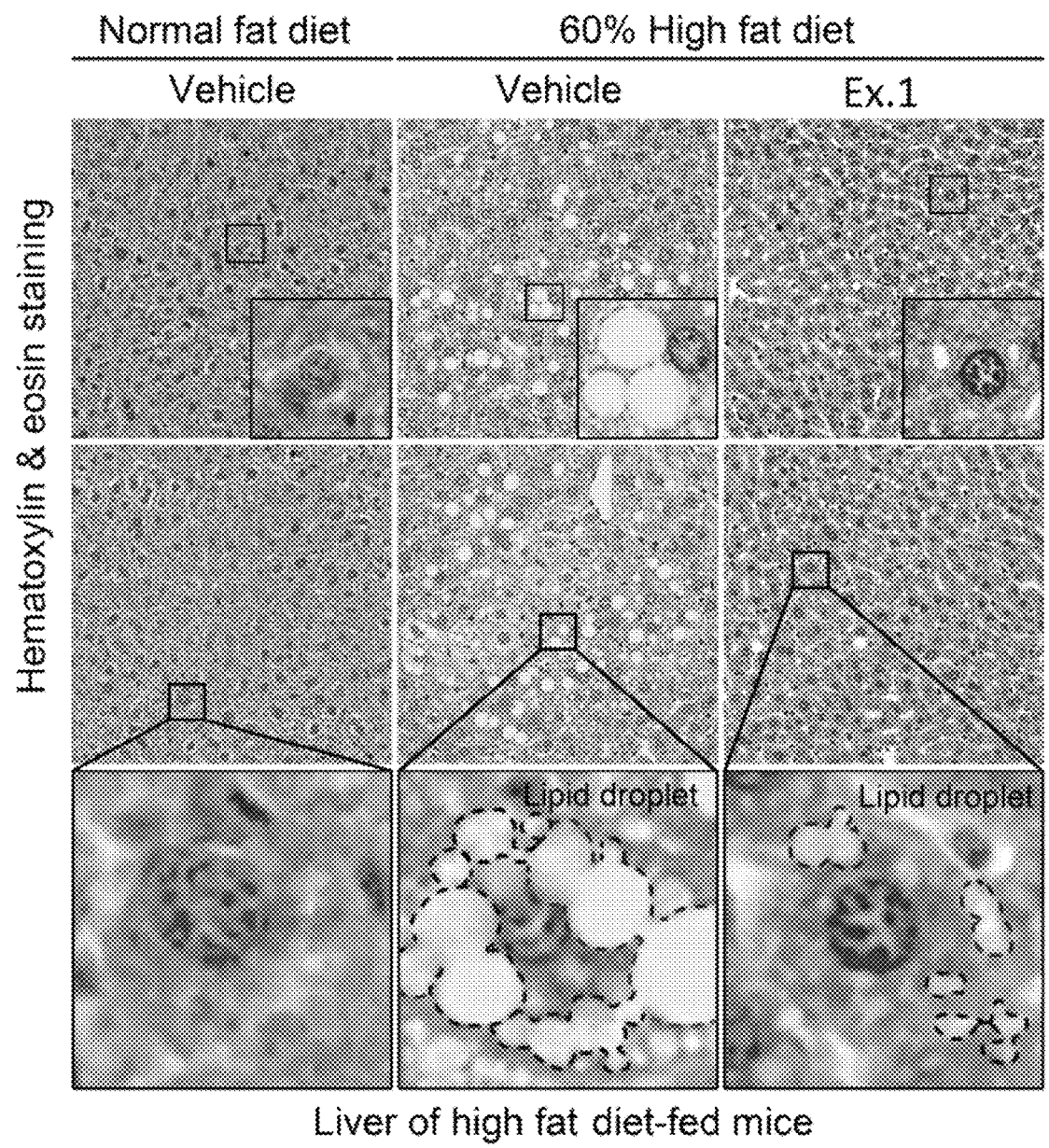

[Fig. 14]
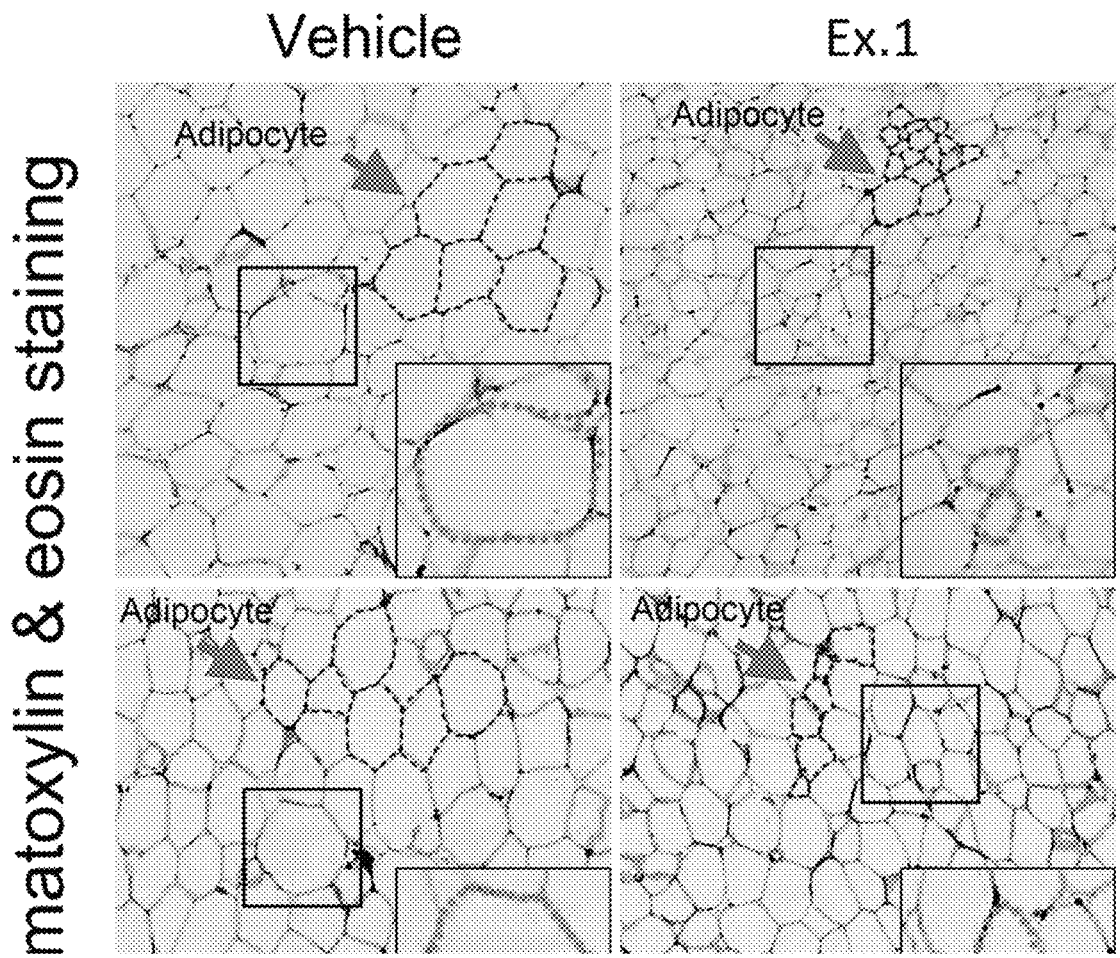

[Fig. 15]
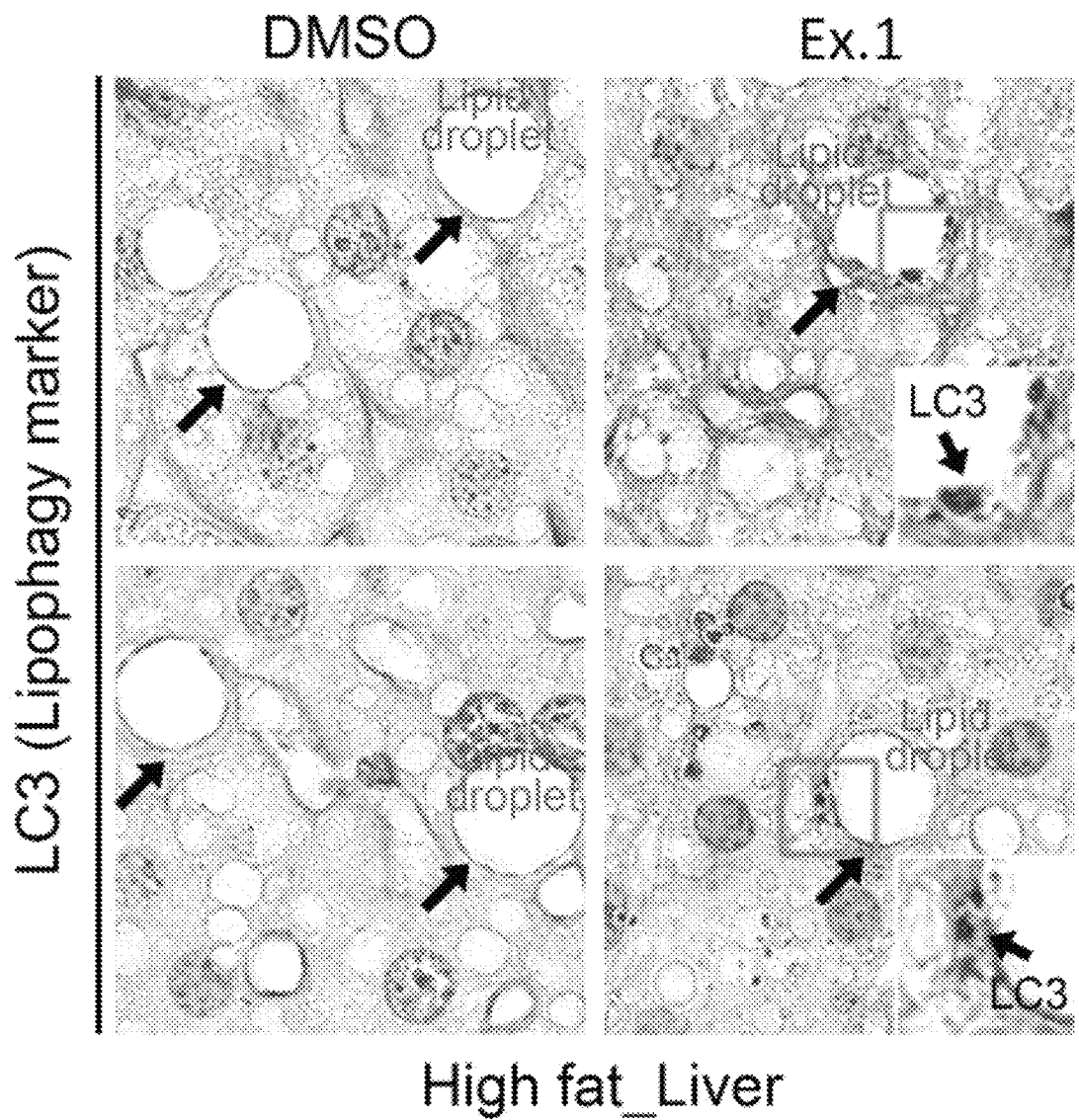

[Fig. 16]
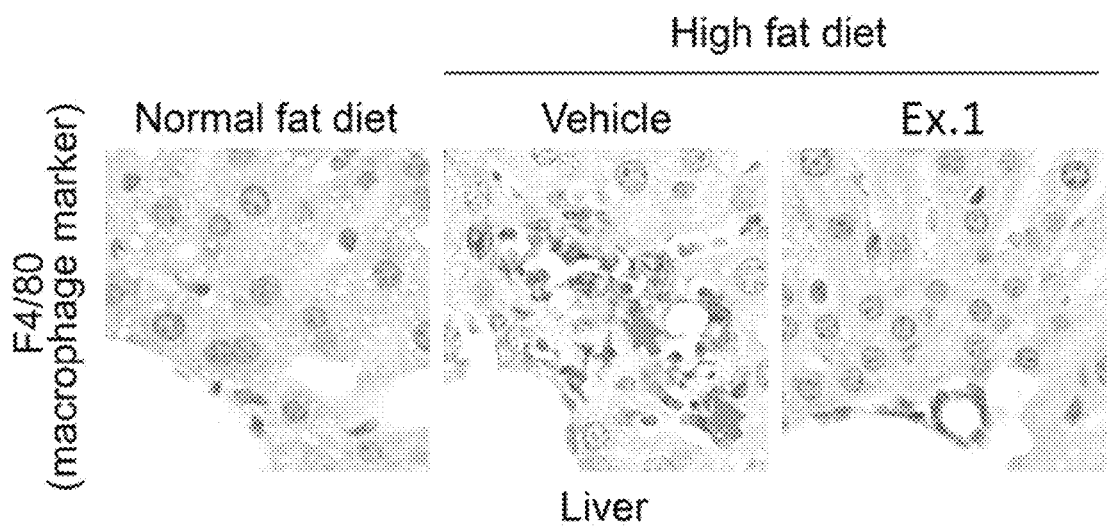

COMPOUND AND PHARMACEUTICAL COMPOSITION FOR PREVENTING OR TREATING OBESITY OR METABOLIC SYNDROME COMPRISING THEREOF

CROSS-REFERENCE TO RELATED APPLICATIONS

This application is a national stage entry of PCT/KR2019/003514 filed Mar. 26, 2019 which claims priority to U.S. Provisional Application No. 62/648,381 filed Mar. 26, 2018, said application is expressly incorporated herein in its entirety.

TECHNICAL FIELD

The present invention relates to a novel compound which can be effectively used for preventing or treating obesity or metabolic syndrome, and a pharmaceutical composition comprising the same.

BACKGROUND ART

Obesity, which was considered as a simple disease, has recently been classified as a disease, and it has been reported that obesity is associated with the onset of metabolic syndrome such as type 2 diabetes, cardiovascular diseases, and certain cancers [1]. Obesity is a disease that results from a combination of various causes such as socio-environmental, genetic, psychiatric and endocrine factors. According to the World Health Organization (WHO), the worldwide prevalence of obesity has increased by double since 1980 [2], and in the United States, approximately 34% of American were obese in 2013 [3]. It is the fact that the US government uses 10% of the total national medical expenses for obesity-related health care services, campaigns, etc. every year in order to reduce socioeconomic losses caused by obesity. In recent years, the obesity rates in Asian and African countries also have conspicuously increased. According to 'The Lancet', British medical journal, more than 90 million people in China were obese [4]. The WHO recognized the seriousness of obesity, and put on the agenda of "Global Strategy on Diet, Physical Activity and Health" in May 2004 to focus efforts on reducing overweight and obesity. However, to date, no country in which obesity has decreased has been reported worldwide.

According to McKinsey report, the health care costs associated with obesity in 2012 was approximately $2 trillion [5]. This is much higher than Korea's annual GDP and also higher than the socio-economic costs caused by alcohol consumption. Although obesity is the rising global health issues, only five anti-obesity drugs have been approved for clinical use by the US Food and Drug Administration (FDA) [6].

The mechanism of drugs approved from the US FDA can be divided into three categories: inhibiting lipid absorption in the small intestine through ingested foods, reducing nutrient intake and inducing weight loss by altering the activity of the feeding center in the central nervous system of the brain to induce a fictional sense of fullness, and releasing an energy flowed into the body into a thermal energy without storing it in the form of lipid. However, these drugs can cause side effects associated with metabolic problems such as nutritional imbalance and emotional changes such as lethargy and depression [6].

Thus, the best way for the treatment and prevention of obesity is to remove excess body fat itself that is the causative substance. However, to date, there is no safe and effective treatment to selectively remove excessive accumulated fat except surgical treatment. Therefore, if the problem associated with selective removal of surplus fat without side effects can be solved, it will be possible to reduce the socio-economic costs, etc. caused by obesity beyond the health issues of the individual. In addition, it may be effective in relieving metabolic syndrome such as cardiovascular and cerebrovascular diseases, type 2 diabetes and fatty liver in which obesity is known to be the main cause.

Excessive accumulation of lipid in tissues and blood is the main causes of diverse metabolic syndrome with body weight gain. Abdominal fat increased by a high fat diet affects the body fat and sugar metabolism, and increases triglyceride levels in the blood. Increasing triglyceride levels in the blood causes the accumulation of triglycerides in various tissues. Hepatic disease can be mentioned as a representative metabolic syndrome in which lipid accumulated in tissues is a direct cause of the disease. The accumulation of triglycerides resulting in more 5% of hepatocytes is defined as hepatic steatosis, which can develop into steatohepatitis [7]. Therefore, in order to prevent and treat hepatic diseases, it is the most effective method that effectively removes lipid accumulated in tissues. The main purpose of using drugs to prevent or treat obesity is not simple weight loss, but the goal should be to correct metabolic abnormalities due to accumulated surplus body fat, and ultimately, the focus should be on improving the prognosis of metabolic syndrome, such as diabetes and hepatic diseases, which may be caused by obesity. Therefore, primary goal of anti-obesity drugs should be the selective reduction of accumulated fat without changing the metabolic rate.

To date, there is no compounds that can selectively remove only excess fat accumulated in the body, and research on this is also absent. In order to maintain standard body fat and remove only unnecessary fat, best way to break down the fat it may be the most effective systems that exist to maintain intracellular homeostasis. There exists an autophagy mechanism that decomposes and reuses damaged or unnecessary organelles and constituents such as proteins within cells by using an organ called lysosome. A cell is activated when exposed to a stress situation or put into a nutritional deficiency situation, and the cell utilizes these mechanisms to properly maintain an intracellular environment. Depending on the substrate to be degraded, it is variously classified into Mitophagy, Xenophagy, Lipophagy and the like [8]. Lipophagy system is known to function to remove lipid droplets accumulated in cells, and Mark J. Czaja and Ana Maria Cuervo conducted a joint research project and as a result, published in the 2009 Nature Journal that the lipid droplets accumulated in cells are removed by the action of lipophagy. Thereafter, studies on its mechanism and activation method are actively underway. Therefore, if the lipophagy process can be controlled by a technical method, it can be used as an effective therapeutic agent that can replace existing anti-obesity agents that prevent the lipid accumulation through regulation of feeding patterns and energy metabolism.

Therefore, the present inventors have conducted intensive studies to develop a drug as described above, and as a result, have found that a novel compound described later satisfies the properties as described above, thereby completing the present invention.

REFERENCES

1. Cummings D E, and Schwartz M W. Genetics and pathophysiology of human obesity. *Annu Rev Med* 2003; 54:453-471

2. World Health Organization: Regional for Europe. Obesity [Internet]. Geneva: World Health Organization, c2013 [cited 2013 Mar. 30]. Available from: http://www.euro.who.int/en/what-we-do/healthtopics/noncommunicable-disease/obesity/facts-and-figures.
3. Centers for Disease Control and Prevention. Overweight and Obesity: Adults Obesity Facts [Internet]. Centers for Disease Control and Prevention 2012 [updated 2012; cited 2013 Mar. 6]. Available from http://www.cdc.gov/obesity/data/adult.html.
4. Ng M, Fleming T, Robinson M, Graetz N, Margono C, Mullany E C et al. Global, regional, and national prevalence of overweight and obesity in children and adults during 1980-2013: a systematic analysis for the Global Burden of Disease Study 2013. *The Lancet* 2014; 384: 766-781
5. Dobbs R. et al., Overcoming obesity: An initial economic analysis. McKinsey Global Institute, 2014
6. Daneschvar H L, Smetana G W. FDA-approved anti-obesity drugs in the United States. *The Am J Med* 2016, 129:879.e1-879.e6
7. Kneeman J M, Misdraji J, Corey K E. Secondary cause of nonalcoholic fatty liver disease. *Therap. Adv. Gastroenterol* 2012; 5:199-207
8. Anding A L, Baehrecke E H. Cleaning House: Selective autophagy of organelles. *Developmental cell* 2017; 10:41: 10-22
9. Kaushik S, Cuervo A M. Degradation of lipid droplet-associated proteins by chaperone-mediated autophagy facilitates lipolysis. *Nat cell Biol* 2015; 17:759-770

DETAILED DESCRIPTION OF THE INVENTION

Technical Problem

It is an object of the present invention to provide a novel compound or a pharmaceutically acceptable salt thereof which can be effectively used for preventing or treating obesity or metabolic syndrome, and a pharmaceutical composition comprising the same.

Technical Solution

In order to achieve the above objects, the present invention provides a compound represented by the following Chemical Formula 1 or a pharmaceutically acceptable salt thereof.

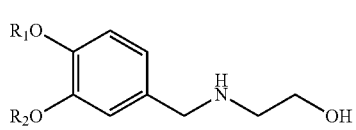

[Chemical Formula 1]

in Chemical Formula 1,
$R_1$ is -$L_1$-(phenyl),
$R_2$ is hydrogen, or -$L_2$-(phenyl),
$L_1$ is $C_{1-5}$ alkylene, and
$L_2$ is $C_{1-5}$ alkylene,
with the proviso that not both $R_1$ and $R_2$ are benzyl.
Preferably, $L_1$ is a linear $C_{1-5}$ alkylene. More preferably, $L_1$ is —$CH_2$—, —$CH_2CH_2$—, —$CH_2CH_2CH_2$—, or —$CH_2CH_2CH_2CH_2$—.

Preferably, $L_2$ is a linear $C_{1-5}$ alkylene. More preferably, $L_2$ is —$CH_2$—, —$CH_2CH_2$—, —$CH_2CH_2CH_2$—, or —$CH_2CH_2CH_2CH_2$—.

Preferably, $R_1$ is —$CH_2$-(phenyl), and $R_2$ is hydrogen, —$CH_2CH_2$-(phenyl), —$CH_2CH_2CH_2$-(phenyl), or —$CH_2CH_2CH_2CH_2$-(phenyl).

Preferably, $R_1$ and $R_2$ are equal to each other. More preferably, $R_1$ and $R_2$ are —$CH_2CH_2$-(phenyl), —$CH_2CH_2CH_2$-(phenyl), or —$CH_2CH_2CH_2CH_2$-(phenyl).

Representative examples of the compound represented by Chemical Formula 1 are as follows:
1) 2-(3,4-diphenethoxybenzylamino)ethanol,
2) 2-(3,4-bis(3-phenylpropoxy)benzylamino)ethanol,
3) 2-(3,4-bis(4-phenylbutoxy)benzylamino)ethanol,
4) 2-(benzyloxy)-5-((2-hydroxyethylamino)methyl)phenol,
5) 2-(4-(benzyloxy)-3-phenethoxybenzylamino)ethanol,
6) 2-(4-(benzyloxy)-3-(3-phenylpropoxy)benzylamino)ethanol, and
7) 2-(4-(benzyloxy)-3-(4-phenylbutoxy)benzylamino)ethanol.

Meanwhile, the compounds represented by Chemical Formula 1 above may be used in the form of pharmaceutically acceptable salts; and as the salt, an acid addition salt formed in the form of a pharmaceutically acceptable free acid is useful. The acid addition salt is obtained from inorganic acids such as hydrochloric acid, nitric acid, phosphoric acid, sulfuric acid, hydrobromic acid, hydroiodic acid, azilic acid or phosphorous acid, non-toxic organic acids such as aliphatic mono- or di-carboxylate, phenyl-substituted alkanoates, hydroxyalkanoates or alkanedioates, aromatic acids, aliphatic or aromatic sulfonic acids, and organic acids such as acetic acid, benzoic acid, citric acid, lactic acid, maleic acid, gluconic acid, methanesulfonic acid, 4-toluenesulfonic acid, tartaric acid, fumaric acid. Pharmaceutically non-toxic salts as described above include sulfate, pyrosulfate, bisulfate, sulfide, bisulfide, nitrate, phosphate, monohydrogen phosphate, dihydrogen phosphate, metha-phosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dionate, hexane-1,6-dioate, benzoate, chlorobenzoate, methyl benzoate, di nitrobenzoate, hydroxybenzoate, methoxybenzoate, phthalate, terephthalate, benzenesulfonate, toluenesulfonate, chlorobenzene sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate, and the like.

The acid addition salt may be prepared by a conventional method. For example, the acid addition salt may be prepared by dissolving the amino acid derivative of Chemical Formula 1 in an organic solvent such as methanol, ethanol, acetone, dichloromethane, acetonitrile, or the like, adding an organic or inorganic acid, and filtering and drying the produced precipitates, or alternatively distilling a solvent and an excess acid under reduced pressure, followed by drying or crystallization in the presence of an organic solvent.

In addition, a pharmaceutically acceptable metal salt may be prepared using a base. An alkaline metal or alkaline earth metal salt may be prepared, for example, by dissolving the compound in an excessive amount of an alkaline metal hydroxide or alkaline earth metal hydroxide solution, filtering non-dissolved compound salts, and then evaporating and drying the filtrate. In this case, it is pharmaceutically suitable to prepare a sodium, potassium, or calcium salt as the metal salt. In addition, a salt corresponding thereto may be obtained by reacting the alkaline metal or alkaline earth metal salt with a suitable silver salt (for example, silver nitrate).

Further, the present invention includes not only the compound expressed in Chemical Formula 1 and the pharmaceutically acceptable salt thereof but also all of the solvates, optical isomers, hydrates, and the like, capable of being prepared from therefrom.

Further, the present invention provides, for example, a process for preparing a compound represented by Chemical Formula 1 as shown in the following Reaction Scheme 1.

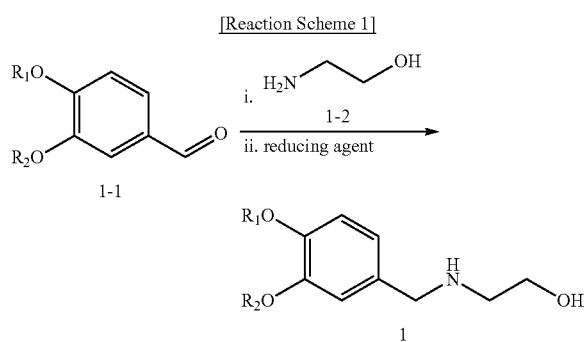

[Reaction Scheme 1]

In Reaction Scheme 1, $R_1$ and $R_2$ are the same as defined above.

The reaction is a reaction for preparing the compound represented by Chemical Formula 1 by reacting the compound represented by Chemical Formula 1-1 and the compound represented by Chemical Formula 1-2, and is substantially composed of two steps. Specifically, the compound represented by Chemical Formula 1-1 is reacted with the compound represented by Chemical Formula 1-2 to prepare an imine compound, wheic which is then reduced to prepare the compound represented by Chemical Formula 1.

The solvent that can be used in the above reaction may be water, ethanol, tetrahydrofuran, dichloromethane, toluene, or acetonitrile, without being restricted thereto. Also, the reaction temperature is not particularly limited, but the reaction may be performed at 10° C. to 90° C., preferably 10° C. to 30° C. or 60° C. to 80° C. Further, the reducing agent is not particularly limited, and $NaBH_4$ may be used as an example. In addition, after the reaction, a purification step may be included as needed.

Further, the present invention provides a pharmaceutical composition for preventing or treating obesity or metabolic syndrome, comprising the compound represented by Chemical Formula 1 or a pharmaceutically acceptable salt thereof.

As confirmed in the experimental examples described later, it was found that the compounds according to the present invention selectively decomposes lipid droplets accumulated excessively in adipocytes to reduce the size of accumulated lipid droplets, through Oil Red-O staining method. Further, as confirmed in the weight loss effect of the compound of the present invention in high-fat diet-fed mice, when injected intraperitoneally in high-fat diet induced obese mice, a statistically significant level of weight loss effect was confirmed compared to control drug-treated mice.

These results demonstrate that the compounds according to the present invention can selectively reduce or eliminate only adipocytes which have been excessively accumulated, that it, adipocytes which may be a cause for inducing diseases. Therefore, the compounds according to the present invention can be an effective alternative to previous drugs that are concerned about the occurrence of side effects by inducing an increase in energy consumption or a change of feeding style through changes in metabolic processes.

Examples of the metabolic syndromes include any one selected from the group consisting of myocardial infarction, arteriosclerosis, hyperlipidemia, hypertension, cerebral infarction, cerebral hemorrhage, fatty liver, and type 2 diabetes mellitus. Such a metabolic syndrome acts as the major cause of obesity due to the decrease in physical activity, in addition to the intake of high-fat diets, and is a disease accompanied by metabolic abnormalities such as increased body fat, blood pressure elevation, and blood lipid abnormality. Thus, the treatment or prevention of obesity through the removal of excessive accumulated body fat may be effective in improving the prognosis of the metabolic syndrome.

The term "prevention" used herein refers to all the activities of inhibiting or delaying occurrence, spread or recurrence of the above-mentioned diseases by the administration of the pharmaceutical composition of the present invention, and the term "treatment" refers to all the activities of improving or changing the symptoms of the above diseases for the better by the administration of the pharmaceutical composition of the present invention.

The pharmaceutical compositions according to the present invention may be formulated in an oral administration form or a parenteral administration form according to standard pharmaceutical practice. The dosage forms may contain additives such as pharmaceutically acceptable carrier, adjuvant, or diluents, in addition to the active ingredient. The suitable carrier may include, for example, a saline solution, polyethyleneglycol, ethanol, vegetable oil and isopropyl myristate, and the like, the diluents may include, for example, lactose, dextrose, sucrose, mannitol, sorbitol, celluolose and/or glycine, and the like, without being limited thereto. And, the compounds of the present invention may be dissolved in oil commonly used for preparing an injection solution, propyleneglycol or other solvents. And, for local action, the compound of the present invention may be formulated into an ointment or cream. And, for local administration, the compound of the present invention may be formulated into ointment, gel or cream.

Preferable administration amount of the compound of the present invention is varied according to the condition and body weight of a patient, the severity of disease, the form of drug, administration route and period, but may be appropriately selected by a person of ordinary skill in the art. However, in order to achieve preferable effect, it is preferable to administer the compound represented by Chemical Formula 1 according to the present invention in an amount of 0.0001 to 100 mg/kg (body weight), preferably 0.001 to 100 mg/kg (body weight) per day. It may be administered orally or parenterally once a day or in divided doses.

According to the administration method, the pharmaceutical composition according to the present invention may contain 0.001 to 99 wt %, preferably 0.01 to 60 wt % of the compound represented by Chemical Formula 1 according to the present invention or a pharmaceutically acceptable salt thereof.

The pharmaceutical composition of the present invention may be administered to mammals including rat, mouse, domestic animals and human being through various routes. All modes of administration may be expected, and for example, it may be administered orally, rectally, or by intravenous, intramuscular, subcutaneous, intrauterine or intracerbroventricular injection.

Advantageous Effects

As described above, the compound or a pharmaceutically acceptable salt thereof according to the present invention can be effectively used for preventing or treating obesity or metabolic syndrome.

BRIEF DESCRIPTION OF THE DRAWINGS

FIG. 1 and FIG. 2 show results confirming the effects of decreasing the lipid droplet size in 3T3-L1 adipocytes and Hep G2 hepatocytes by the compounds of the present invention through Oil Red O staining FIG. 3 shows the results confirming the effects of decreasing the lipid droplet size and number in 3T3-L1 adipocytes by the compounds of the present invention through BODIPY staining.

FIG. 4 shows the results confirming a phenomenon in which the compounds of the present invention activate the lipophagy process in 3T3-L1 adipocytes (FIG. 4A) and Hep G2 hepatocytes (FIG. 4B) and the activated lipophagy process decreases the size and number of lipid droplets accumulated in cells, through the immunofluorescence staining.

FIG. 5 shows the results confirming that treatment of the compounds of the present invention and Bafilomycin as an inhibitor of the action of lipophagy together did not result in removal of lipid droplets, in order to verify that the compounds of the present invention had removed the lipid droplets through the lipophagy process.

FIG. 6 shows the results confirming that in order to confirm the anti-obesity effect of the compounds of the present invention at the living body level, obesity was induced in wild-type mice via high-fat diets, and the body weight and abdominal adipose tissue size were reduced after treatment of the placebo and the compounds of the present invention.

FIG. 7 shows the result recording the changes in body weight weekly by the treatment of the placebo and the compound of the present invention.

FIG. 8 is a graph showing the measurement results of the weight of each tissue in order to confirm that the weight loss effect exhibited by the treatment of the compound of the present invention was caused by a decrease in the adipose tissue weight.

FIG. 9 is a graph showing the results of comparison of the weights of adipose tissues reduced by the compounds of the present invention.

FIG. 10 is a photograph comparing the actual appearance of each tissue extracted to confirm that the weight of the adipose tissue alone has reduced. In each photograph, the left side was one treated with the vehicle, and the right side was one treated with the compound of the present invention.

FIG. 11 is a graph showing the percentage of the body weight reduced through the compounds of the present invention. In addition, the results of measurement of the body height was shown to compare the degree of development during the administration period. In order to determine whether the weight loss effect was due to a decrease in feed intake, the results of surveying feed intake were shown.

FIG. 12 shows the results of the items that have examined blood samples taken from the placebo-treated mice and the compound-administered mice in order to understand that the weight loss caused by the compounds of the present invention has an effect on blood lipid components, blood glucose and pathological conditions of the tissue.

FIG. 13 shows the results of observation of mouse adipose tissues through HnE staining in order to confirm the removal effect of lipid droplets accumulated in the tissues by the compounds of the present invention.

FIG. 14 shows the result of observation of mouse adipose tissue through HnE staining in order to confirm that the size of adipocytes was reduced by the compound of the present invention.

FIG. 15 shows the results confirming the improvement of the expression of LC3 protein as a marker of lipophagy activity through tissue immunochemical staining in order to confirm that the weight loss and the lipid droplet-reducing effects exhibited by the compounds of the present invention were caused by the action of lipophagy.

FIG. 16 shows the results of observation of the expression patterns of macrophages, which are inflammatory cells, through tissue immunochemical staining in order to observe the relaxation effect of the compounds of the present invention against inflammatory symptoms in hepatic tissues caused by excessive accumulation of lipid droplets.

DETAILED DESCRIPTION OF THE EMBODIMENTS

Hereinafter, the present invention will be described in detail with reference to the following Examples and Experimental Examples. However, these Examples and Experimental Examples are presented for illustrative purposes only, and the scope of the invention is not limited thereto.

Example 1: Preparation of 2-(3,4-diphenethoxybenzylamino)ethanol Hydrochloride

Step 1) Preparation of 3,4-diphenethoxybenzaldehyde and 3-hydroxy-4-phenethoxybenzaldehyde

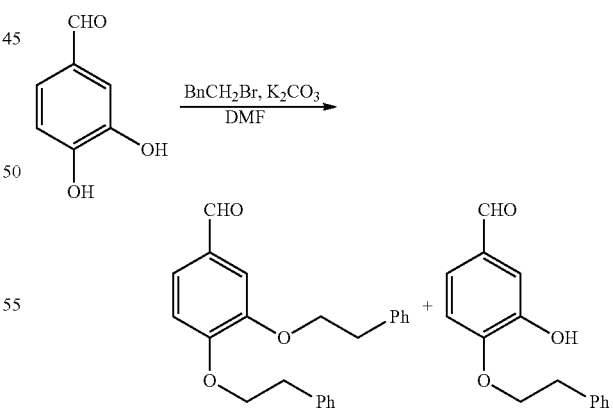

A solution of 3,4-dihydroxybenzaldehyde (0.50 g, 3.62 mmol) was diluted with DMF (10 mL) and stirred. (2-Bromoethyl) benzene (1.24 mL, 9.05 mmol) was slowly added and anhydrous $K_2CO_3$ (2.5 g, 18.1 mmol) was added. The mixture was stirred at room temperature for 2 hours, and $K_2CO_3$ (2.4 g, 17.3 mmol) was further added, heated to 70° C. for 30 minutes and then cooled to room temperature. The mixture was partitioned between water (120 mL) and ether (120 mL). The organic layer was separated and the aqueous layer was extracted with ether (3×50 mL). The extracted organic layer was washed with water (2×50 mL) and saturated with aqueous NaCl solution (50 mL). The light pale yellow extract was dried over anhydrous sodium sulfate, washed with hexane (75 mL) and then concentrated. The resulting residue was purified by silica gel column chromatography using ethyl acetate:hexane (1:4) to give 3,4-diphenethoxybenzaldehyde (6.57 g, 95%) as a cream-colored solid and 3-hydroxy-4-phenethoxybenzaldehyde as a cream-colored solid, respectively.

3-Hydroxy-4-phenethoxybenzaldehyde: $^1$H-NMR (CDCl$_3$, 300 MHz): δ 9.78 (s, 1H), 7.22-7.40 (m, 12H), 6.91 (d, 1H, J=6.0 Hz), 4.23 (td, 4H, J=3.0 and 6.0 Hz), 3.15 (td, 4H, J=3.0 and 6.0 Hz); ESI MS: m/z 243.17 [M+H]$^+$ 3,4-diphenethoxybenzaldehyde: $^1$H-NMR (CDCl$_3$, 300 MHz): δ 9.84 (s, 1H), 7.26-7.43 (m, 7H), 6.96 (d, 1H, J=9.0 Hz), 5.62 (s, 1H), 4.36 (t, 2H, J=6.0 Hz), 3.17 (t, 2H, J=6.0 Hz); ESI MS: m/z 347.33 [M+H]$^+$ Step 2) Preparation of 2-(3,4-diphenethoxybenzylamino)ethanol

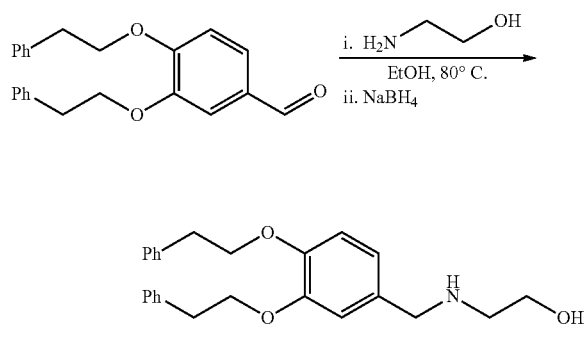

2-Aminoethanol (27 mg (27 μL), 0.45 mmol) was added to 3,4-diphenethoxybenzaldehyde (100 mg, 0.3 mmol) prepared in the previous step 1 in ethanol (5 mL) while stirring them. The mixture was stirred at 80° C. for 12 hours and then cooled to room temperature. NaBH$_4$ (17 mg, 0.45 mmol) was added and further stirred for 12 hours. The solvent was evaporated in vacuo and the residue was dissolved in water and then extracted with ethyl acetate. The organic layer was combined, dried over Na$_2$SO$_4$ and evaporated in vacuo. The residue was purified by flash column to give 2-(3,4-diphenethoxybenzylamino)ethanol (96 mg, 85%).

ESI MS: m/z 392.92 [M+H]$^+$

Step 3) Preparation of 2-(3,4-diphenethoxybenzylamino)ethanol Hydrochloride 2-(3,4-Diphenethoxybenzylamino)ethanol (1.0 g, 2.75 mmol) prepared in the previous step 2 was dissolved in methanol (25 mL) and HCl gas was introduced for 1 hour. The mixture was further stirred for 2 hours and evaporated to about 1 mL, and then hexane was added to prepare a solid, which was then filtered and dried to give the final compound 2-(3,4-diphenethoxybenzylamino)ethanol hydrochloride (720 mg, 65%).

Example 2: Preparation of 2-(3,4-bis(3-phenylpropoxy)benzylamino)ethanol hydrochloride Step 1) Preparation of 3,4-bis(3-phenylpropoxy)benzaldehyde

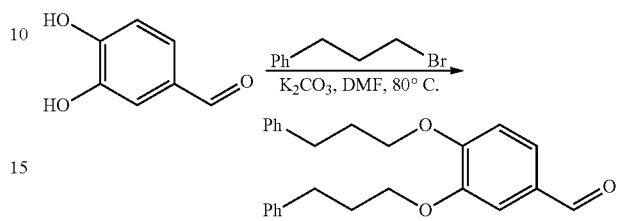

3,4-Dihydroxybenzaldehyde (500 mg, 3.62 mmol) was diluted with DMF (10 mL), and anhydrous K$_2$CO$_3$ (1.5 g, 10.86 mmol) and (3-bromopropyl)benzene (1.2 mL, 7.96 mmol) were slowly added in this order. The mixture was heated to 80° C. and stirred for 2 hours and then cooled to room temperature. The mixture was partitioned between water (50 mL) and ether (50 mL). The organic layer was separated and the water was extracted with ether (3×50 mL). The extracted organic layer was washed with water (2×50 mL) and saturated with aqueous NaCl solution (50 mL). The light pale yellow extract was dried over anhydrous sodium sulfate, washed with hexane (75 mL) and then concentrated. The resulting residue was purified by silica gel column chromatography using ethyl acetate:hexane (1:4) to give 3,4-bis(3-phenylpropoxy)benzaldehyde (1.3 g, 96%) as a cream-colored solid.

$^1$H-NMR (CDCl$_3$, 300 MHz): δ 9.86 (s, 1H), 7.45 (dd, 1H, J=3.0 and 9.0 Hz), 7.41 (d, 1H, J=3.0 Hz), 7.22-7.34 (m, 10H) 6.95 (d, 1H, J=9.0 Hz), 4.12 (td, 4H, J=3.0 and 9.0 Hz), 2.87 (td, 4H, J=3.0 and 9.0 Hz), 2.17-2.28 (m, 4H).

Step 2) Preparation of 2-(3,4-bis(3-phenylpropoxy)benzylamino)ethanol

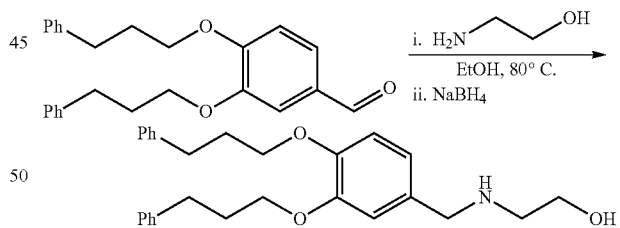

2-Aminoethanol (25 mg (25 μL), 0.40 mmol) was added to 3,4-bis(3-phenylpropoxy)benzaldehyde (100 mg, 0.27 mmol) prepared in the previous step 1 in ethanol (5 mL) while stirring them, and the mixture was stirred at 60° C. for 12 hours. The reaction solution was cooled to room temperature. NaBH$_4$ (15.2 mg, 0.40 mmol) was slowly added, and further stirred for 12 hours. The solvent was evaporated in vacuo and the residue was dissolved in water and then extracted with ethyl acetate. The organic layer was combined, dried over Na$_2$SO$_4$, and then filtered and evaporated in vacuo. The residue was purified by flash column to give 2-(3,4-bis(3-phenylpropoxy)benzylamino)ethanol (96 mg, 86%).

ESI MS: m/z 421.0 [M+2H]$^+$

Step 3) Preparation of 2-(3,4-bis(3-phenylpropoxy)-benzylamino)ethanol Hydrochloride 2-(3,4-bis(3-phenylpropoxy)benzylamino)ethanol (1.0 g, 2.75 mmol) prepared in the previous step 2 was dissolved in methanol (25 mL) and HCl gas was introduced for 1 hour. The mixture was further stirred for 2 hours and evaporated to about 1 mL, and then hexane was added to prepare a solid, which was then filtered and dried to give 2-(3,4-bis(3-phenylpropoxy)-benzylamino)ethanol hydrochloride (720 mg, 65%).

Example 3: Preparation of 2-(3,4-bis(4-phenylbutoxy)benzylamino)ethanol

Step 1) Preparation of 3,4-bis(4-phenylbutoxy)benzaldehyde

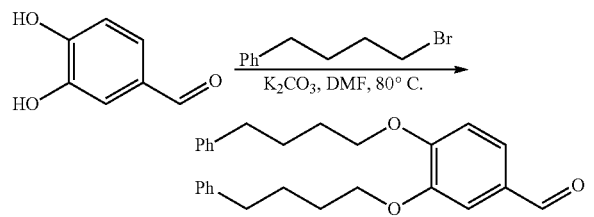

3,4-Dihydroxybenzaldehyde (147 mg, 1.07 mmol) was diluted with DMF (10 mL), and anhydrous $K_2CO_3$ (442 mg, 3.20 mmol) and (4-bromobutyl)benzene (0.4 mL, 2.35 mmol) were slowly added in this order. The mixture was heated to 80° C. and stirred for 2 hours and then cooled to room temperature. The mixture was partitioned between water (50 mL) and ether (50 mL). The organic layer was separated and the water was extracted with ether (3×50 mL). The extracted organic layer was washed with water (2×50 mL) and saturated with aqueous NaCl solution (50 mL). The light pale yellow extract was dried over anhydrous sodium sulfate, washed with hexane (75 mL) and then concentrated. The resulting residue was purified by silica gel column chromatography using methanol (1% to 5% in DCM) to give 3,4-bis(4-phenylbutoxy)benzaldehyde (398 mg, 93%) as a cream-colored solid.

$^1$H-NMR (CDCl$_3$, 300 MHz): δ 7.46-7.26 (m, 10H), 6.84 (d, 1H, J=9.0 Hz), 6.59 (d, 1H, J=3.0 Hz), 6.38 (dd, 1H, J=3.0 and 9.0 Hz), 5.12 (s, 1H), 5.07 (s, 1H), 4.03 (td, 1H, J=3.6 and 5.1 Hz), 3.93-3.86 (m, 2H), 3.25 (s, 2H), 2.92-2.86 (m, 2H), 2.72 (dd, 1H, J=8.1 and 12.0 Hz), 1.12 (d, 6H, J=6.3 Hz)

ESI MS m/z: 496 [M+H]$^+$

Step 2) Preparation of 2-(3,4-bis(4-phenylbutoxy)benzylamino)ethanol

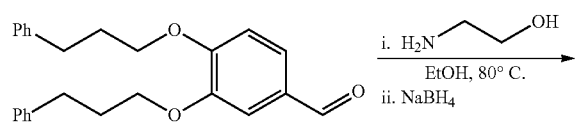

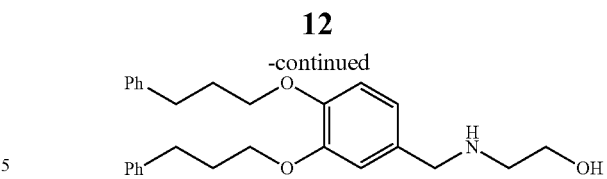

2-Aminoethanol (106 mg, 1.74 mmol) was added to 3,4-bis(4-phenylbutoxy)benzaldehyde (0.35 g, 0.87 mmol) prepared in the previous step 1 in ethanol (5 mL) while stirring them, and the mixture was stirred at 60° C. for 12 hours. The reaction solution was cooled to room temperature. NaBH$_4$ (33 mg, 0.87 mmol) was slowly added and further stirred for 12 hours. The solvent was evaporated in vacuo and the residue was dissolved in water and then extracted with ethyl acetate. The organic layer was combined, dried over Na$_2$SO$_4$, and then filtered and evaporated in vacuo. The residue was purified by flash column to give 2-(3,4-bis(4-phenylbutoxy)benzylamino)ethanol (0.33 g, 85%).

ESI MS: m/z 449.0 [M+2H]$^+$

Example 4: Preparation of 2-(benzyloxy)-5-((2-hydroxyethylamino)methyl)phenol Hydrochloride

Step 1) Preparation of 4-benzyloxy-3-hydroxybenzaldehyde

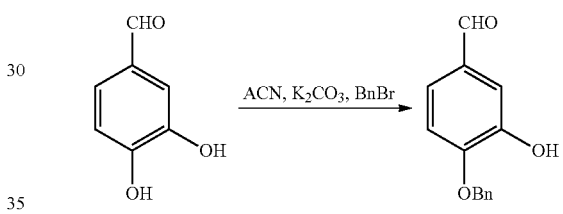

$K_2CO_3$ (2.5 g, 18.1 mmol) was added to a solution of 3,4-dihydroxybenzaldehyde (2.5 g, 18.1 mmol) in anhydrous acetonitrile (30 mL) at room temperature under an inert gas (N$_2$) atmosphere while stirring them, and benzyl bromide (3.44 mL, 29.0 mmol) was slowly added. The mixture was heated to reflux and stirred for 2 hours to perform the reaction. The reaction solvent was removed by evaporation under reduced pressure, and to the result was added a cold 10% NaOH solution and stirred for 10 minutes, and then ethyl acetate (100 mL) was added. The resulting biphasic mixture was separated and the aqueous layer was acidified with 4N HCl and extracted with DCM (3×300 mL). The organic layer was washed with brine, and water, dried over Na$_2$SO$_4$ and concentrated under reduced pressure to give a residue, which was purified by crystallization from ethyl acetate to give 4-benzyloxy-3-hydroxybenzaldehyde (2.90 g, 70%) as a white powder.

$^1$H NMR (300 MHz, CDCl$_3$): δ 9.83 (s, 1H, CHO), 7.39-7.46 (m, 7H, ArH), 7.03 (d, 1H, J=9.0 Hz, ArH), 5.88 (s, 1H, OH), 5.20 (s, 2H, OCH$_2$Ph)

ESI MS: m/z 229.25 [M+H]$^+$

Step 2) Preparation of 2-(benzyloxy)-5-((2-hydroxyethylamino)methyl)phenol

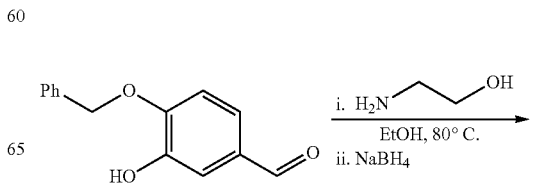

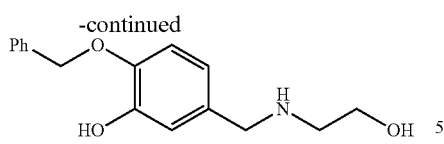

2-Aminoethanol (81 mg (80 μL), 1.32 mmol) was added to 4-(benzyloxy)-3-hydroxybenzaldehyde (200 mg, 0.88 mmol) prepared in the previous step 1 in ethanol (5 mL) while stirring them, and the mixture was stirred at 60° C. for 12 hours and then cooled to room temperature. NaBH₄ (50 mg, 1.32 mmol) was slowly added and further stirred for 12 hours. The solvent was evaporated in vacuo and the residue was dissolved in water and then extracted with ethyl acetate. The organic layer was combined, dried over Na₂SO₄, and then filtered and evaporated in vacuo. The residue was purified by flash column to give 2-(benzyloxy)-5-((2-hydroxyethylamino)methyl)phenol (0.22 g, 92%).

ESI MS: m/z 274.75 [M+H]⁺

Step 3) Preparation of 2-(benzyloxy)-5-((2-hydroxyethylamino)methyl)phenol Hydrochloride 2-(Benzyloxy)-5-((2-hydroxyethylamino)methyl)phenol (1.0 g, 2.75 mmol) prepared in the previous step 2 was dissolved in methanol (25 mL) and HCl gas was introduced for 1 hour. The mixture was stirred for 2 hours and evaporated to about 1 mL, and then hexane was added to prepare a solid, which was then filtered and dried to give 2-(benzyloxy)-5-((2-hydroxyethylamino)methyl)phenol hydrochloride (720 mg, 65%).

Example 5: Preparation of 2-(4-(benzyloxy)-3-phenethoxybenzylamino)ethanol Hydrochloride

Step 1) Preparation of 4-(benzylbenzyloxy)-3-phenoxybenzaldehyde

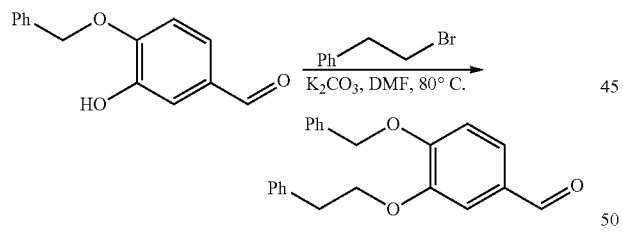

4-(Benzylbenzyloxy)-3-hydroxybenzaldehyde (0.50 g, 2.19 mmol) was diluted with DMF (10 mL), and anhydrous K₂CO₃ (604 mg, 4.38 mmol) and (2-bromoethyl)benzene (0.36 mL, 2.63 mmol) were slowly added in this order. The mixture was heated at 70° C. for 2 hours and then cooled to room temperature. The mixture was partitioned between water (20 mL) and ether (20 mL). The organic layer was separated and the aqueous layer was extracted with ether (3×20 mL). The extracted organic layer was washed with water (2×20 mL) and saturated with aqueous NaCl solution (20 mL). The light pale yellow extract was dried over anhydrous sodium sulfate and then concentrated. The resulting residue was purified by silica gel column chromatography using ethyl acetate:hexane (1:9) to give 4-(benzylbenzyloxy)-3-phenoxybenzaldehyde (0.66 g, 90%) as a cream-colored solid.

¹H-NMR (CDCl₃, 300 MHz): δ 9.80 (s, 1H), 7.21-7.39 (m, 12H), 6.98 (d, 1H, J=6.0 Hz), 5.17 (s, 2H), 4.27 (t, 2H, J=6.0 Hz), 3.14 (t, 2H, J=6.0 Hz)

Step 2) Preparation of 2-(4-(benzyloxy)-3-phenethoxybenzylamino)ethanol

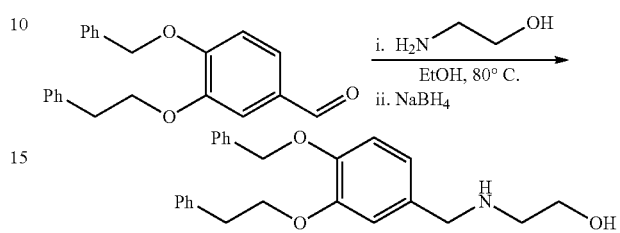

2-Aminoethanol (22 mg (22 μL), 0.36 mmol) was added to a solution of 4-(benzylbenzyloxy)-3-phenoxybenzaldehyde (100 mg, 0.30 mmol) prepared in the previous step 1 in ethanol (5 mL) while stirring them. The reaction mixture was stirred at 60° C. for 12 hours and cooled to room temperature. NaBH₄ (17.1 mg, 0.45 mmol) was slowly added while stirring, and further stirred for 12 hours. The solvent was evaporated in vacuo and the residue was dissolved in water and then extracted with ethyl acetate. The organic layer was combined, dried over Na₂SO₄ and then filtered and evaporated in vacuo. The residue was purified by flash column to give 2-(4-(benzyloxy)-3-phenethoxybenzylamino)ethanol (0.10 g, 90%).

ESI MS: m/z 378.9 [M+H]⁺

Step 3) Preparation of 2-(4-(benzyloxy)-3-phenethoxybenzylamino)ethanol Hydrochloride 2-(4-(benzyloxy)-3-phenethoxybenzylamino)ethanol (1.0 g, 2.75 mmol) prepared in the previous step 2 was dissolved in methanol (25 mL) and HCl gas was introduced for 1 hour. The mixture was stirred for 2 hours and evaporated to about 1 mL, and then hexane was added to prepare a solid, which was then filtered and dried to give 2-(4-(benzyloxy)-3-phenethoxybenzylamino)ethanol hydrochloride (720 mg, 65%).

Example 6: Preparation of 2-(4-(benzyloxy)-3-(3-phenylpropoxy)benzylamino)ethanol Hydrochloride

Step 1) Preparation of 4-(benzylbenzyloxy)-3-(3-phenylpropoxy)benzaldehyde

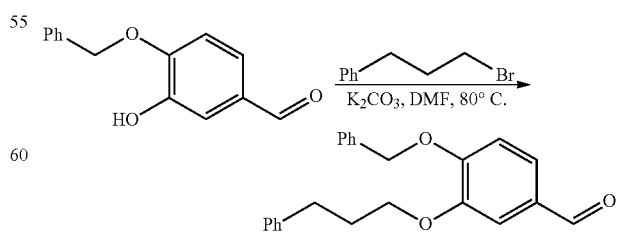

4-(Benzylbenzyloxy)-3-hydroxybenzaldehyde (0.50 g, 2.19 mmol) was diluted with DMF (10 mL), and anhydrous K₂CO₃ (604 mg, 4.38 mmol) and (2-bromopropyl)benzene (0.4 mL, 2.63 mmol) were slowly added in this order. The mixture was heated at 70° C. for 2 hours and then cooled to room temperature. The mixture was partitioned between water (20 mL) and ether (20 mL). The organic layer was separated and the aqueous layer was extracted with ether (3×20 mL). The extracted organic layer was washed with water (2×20 mL) and saturated with aqueous NaCl solution (20 mL). The light pale yellow extract was dried over anhydrous sodium sulfate and then concentrated. The resulting residue was purified by silica gel column chromatography using ethyl acetate:hexane (1:9) to give 4-(benzylbenzyloxy)-3-(3-phenylpropoxy)benzaldehyde (0.68 g, 90%) as a cream-colored solid.

¹H-NMR (CDCl₃, 300 MHz): δ 9.81 (s, 1H), 7.18-7.38 (m, 12H), 7.00 (d, 1H, J=9.0 Hz), 5.23 (s, 2H), 4.09 (t, 2H, J=6.0 Hz), 3.14 (t, 2H, J=6.0 Hz), 2.12-2.22 (m, 2H)

Step 2) Preparation of 2-(4-(benzyloxy)-3-(3-phenylpropoxy)benzylamino)ethanol

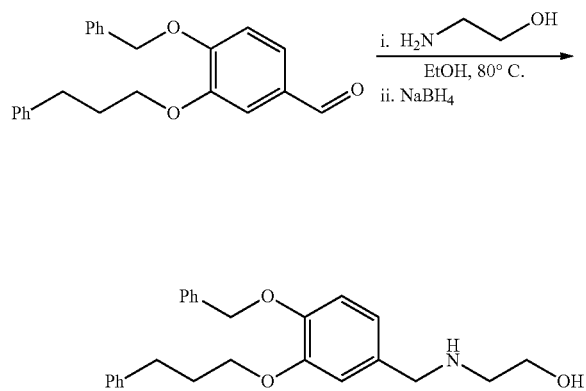

2-Aminoethanol (22 mg (22 μL), 0.36 mmol) was added to 4-(benzylbenzyloxy)-3-(3-phenylpropoxy)benzaldehyde (100 mg, 0.29 mmol) prepared in the previous step 1 in ethanol (5 mL) while stirring them. The reaction mixture was stirred at 60° C. for 12 hours and then cooled to room temperature. NaBH₄ (16.7 mg, 0.44 mmol) was slowly added, and further stirred for 12 hours. The solvent was evaporated in vacuo and the residue was dissolved in water and then extracted with ethyl acetate. The organic layer was combined, dried over Na₂SO₄, and then filtered and evaporated in vacuo. The residue was purified by flash column to give 2-(4-(benzyloxy)-3-(3-phenylpropoxy)benzylamino) ethanol (93 mg, 82%).

ESI MS: m/z 392.92 [M+H]⁺

Step 3) Preparation of 2-(4-(benzyloxy)-3-(3-phenylpropoxy)benzylamino)ethanol Hydrochloride 2-(4-(benzyloxy)-3-(3-phenylpropoxy)benzylamino) ethanol (1.0 g, 2.75 mmol) prepared in the previous step 2 was dissolved in methanol (25 mL) and HCl gas was introduced for 1 hour. The mixture was further stirred for 2 hours and evaporated to about 1 mL, and then hexane was added to prepare a solid, which was then filtered and dried to give 2-(4-(benzyloxy)-3-(3-phenylpropoxy)benzylamino) ethanol hydrochloride (720 mg, 65%).

Example 7: Preparation of 2-(4-(benzyloxy)-3-(4-phenylbutoxy)benzylamino)ethanol

Step 1) Preparation of 4-(benzylbenzyloxy)-3-(4-phenylbutoxy)benzaldehyde

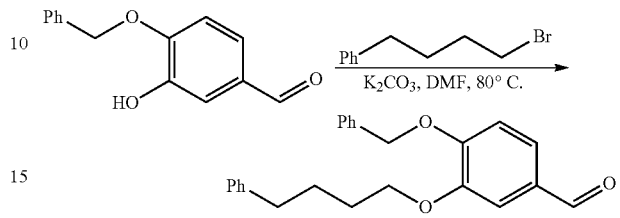

4-(Benzylbenzyloxy)-3-hydroxybenzaldehyde (0.50 g, 2.19 mmol) was diluted with DMF (10 mL), and anhydrous K₂CO₃ (604 mg, 4.38 mmol) and (4-bromopropyl)benzene (0.46 mL, 2.63 mmol) were slowly added in this order. The mixture was heated at 70° C. for 2 hours and then cooled to room temperature. The mixture was partitioned between water (20 mL) and ether (20 mL). The organic layer was separated and the aqueous layer was extracted with ether (3×20 mL). The extracted organic layer was washed with water (2×20 mL) and saturated with aqueous NaCl solution (20 mL). The light pale yellow extract was dried over anhydrous sodium sulfate and then concentrated. The resulting residue was purified by silica gel column chromatography using ethyl acetate:hexane (1:9) to give 4-(benzylbenzyloxy)-3-(4-phenylbutoxy)benzaldehyde (0.69 g, 88%) as a cream-colored solid.

¹H-NMR (CDCl₃, 300 MHz): δ 9.86 (s, 1H), 7.29-7.48 (m, 8H), 7.22-7.24 (m, 3H), 7.03 (d, 1H, J=6.0 Hz), 5.25 (s, 2H), 4.14 (t, 2H, J=6.0 Hz), 2.74 (t, 2H, J=6.0 Hz), 1.87-1.94 (m, 4H)

Step 2) Preparation of 2-(4-(benzyloxy)-3-(4-phenylbutoxy)benzylamino)ethanol

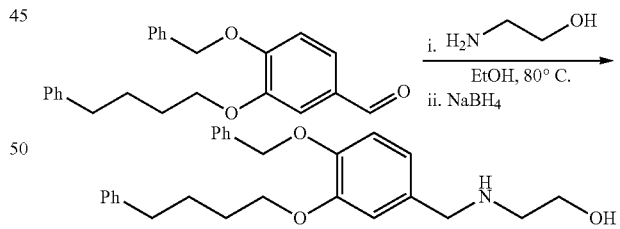

2-Aminoethanol (25.6 mg (25 μL), 0.42 mmol) was added to 4-(benzylbenzyloxy)-3-(4-phenylbutoxy)benzaldehyde (100 mg, 0.28 mmol) prepared in the previous step 1 in ethanol (5 mL) while stirring them. The reaction mixture was stirred at 60° C. for 12 hours and then cooled to room temperature. NaBH₄ (16 mg, 0.42 mmol) was slowly added, and further stirred for 12 hours. The solvent was evaporated in vacuo and the residue was dissolved in water and then extracted with ethyl acetate. The organic layer was combined, dried over Na₂SO₄ and then filtered and evaporated in vacuo. The residue was purified by flash column to give 2-(4-(benzyloxy)-3-(4-phenylbutoxy)benzylamino)ethanol (99 mg, 89%).

¹H NMR (CD₃OD, 300 MHz): δ 7.44-7.41 (m, 2H), 7.32-7.14 (m, 8H), 7.05 (d, 1H, J=1.8 Hz), 7.00 (d, 1H, J=8.1 Hz), 6.90 (dd, 1H, J=1.8 & 8.1 Hz), 5.10 (s, 2H), 4.09-4.05 (m, 2H), 3.90 (s, 2H), 3.72 (t, 2H, J=5.4 Hz), 2.88 (t, 2H, J=5.4 Hz), 2.70-2.65 (m, 2H), 1.85-1.81 (m, 4H)

LC-MS (ESI): m/z 406 (M+H)⁺ and 345 (M−60)⁺

Experimental Example 1: Analysis of the Effect of Decomposing Lipid Droplets in 3T3-L1 Preadipocytes by the Present Compound Through Oil Red O Staining The following experiments were conducted in order to evaluate the effect of decreasing lipid droplets accumulated in cells by the compounds of the present invention.

3T3-L1 preadipocytes were purchased from Korean Cell Line Bank, and cultured and maintained in newborn calf serum (NCS, Invitrogen Corporation, Auckland, New Zealand) and high-glucose DMEM (high glucose Dulbecco's modified Eagle's Medium, Sigma Co., St. Louis, Mo., USA). For adipocyte differentiation, 3T3-L1 with a concentration of 100,000 cells/ml were grown to confluence with 10% fetal bovine serum (FBS) and high-glucose DMEM for 2 days, then cultured in 10% FBS/high-glucose DMEM containing 0.5 mM IBMX (3-isobytyl-1-methyl xanthine), 0.5 μM dexamethasone and 5 μg/ml insulin (MDI) for 2 days, and further cultured in 10% FBS/high-glucose DMEM containing only 5 μg/ml insulin(I) for 4 days, following by again culturing in 10% FBS/high-glucose DMEM alone for another 6 days. Thus, the cells were cultured for a total of 10 days to differentiate into adipocytes. After confluent culture, the cells were treated with the compounds at a concentration of 10 μM each time the medium was changed. On day 10 after differentiation, the cultured cells were fixed with 4% paraformaldehyde and then stained with Oil Red O staining solution. The Oil Red O staining was performed by diluting 0.5 g/200 ml isopropanol stock solution with 60% distilled water, and observed through a microscope at 400× magnification. The results are illustrated in FIG. 1.

In FIG. 1, a red circular structure represents a lipid droplet accumulated in cells. As illustrated in FIG. 1, it shows that the size and number of lipid droplets were reduced by the treatment of the compounds according to the present invention. Therefore, it can be confirmed that the compound according to the present invention is effective for removing lipid droplets in 3T3-L1 preadipocytes.

Experimental Example 2: Analysis of the Effect of Decomposing Lipid Droplets in Hep G2 Cells by the Compound of the Present Invention Through Oil Red O Staining The following experiment was conducted to evaluate the decreasing effect of the present compounds on lipid droplets in cells.

In detail, Hep G2 cells were cultured in DMEM medium supplemented with 10% fetal bovine serum (Hyclone, USA), 100 U/mL penicillin and 100 mg/mL streptomycin (Hyclone, USA). When cells were approximately 50% confluent, the medium was replaced with DMEM medium containing 1 mM oleic acid and 0.5 mM palmitic acid to induce intracellular lipid accumulation, and the cells were cultured for 24 hours. The medium was then replaced with DMEM medium containing 10 μM of each compound synthesized through the present invention and the cells were further cultured for 24 hours. After completion, the cells were fixed with 4% paraformaldehyde for 10 minutes and washed three times with PBS. The cells were then rinsed with 60% isopropanol and then stained with diluted Oil Red O solution (stock solution, 3 mg/mL in isopropanol, working solution, 60% Oil Red O stock solution diluted in water) for 1 hour. The Oil Red O staining was performed by diluting 0.5 g/200 ml isopropanol stock solution with 60% distilled water, and observed through a microscope at a 400× magnification. The results are illustrated in FIG. 2.

In FIG. 2, a red circular structure represents a lipid droplet accumulated in cells. As illustrated in FIG. 2, it shows that the size and number of lipid droplets were reduced by the treatment of the compounds according to the present invention. Therefore, it can be confirmed that the compound according to the present invention had an effect of removing lipid droplets in Hep G2 hepatocytes.

Experimental Example 3: Analysis of the Effect of Decomposing Lipid Droplets in 3T3-L1 and Hep G2 Cells by the Compound of the Present Invention Through BODIPY Staining The following experiment was conducted to evaluate the decreasing effect of the present compounds on lipid droplets in cells by immunofluorescence staining.

3T3-L1 preadipocytes were purchased from Korean Cell Line Bank, and cultured and maintained in newborn calf serum (NCS, Invitrogen Corporation, Auckland, New Zealand) and high-glucose DMEM (high glucose Dulbecco's modified Eagle's Medium, Sigma Co., St. Louis, Mo., USA). For adipocyte differentiation, 3T3-L1 with a concentration of 100,000 cells/ml were grown to confluence with 10% fetal bovine serum (FBS) and high-glucose DMEM for 2 days, then cultured in 10% FBS/high-glucose DMEM containing 0.5 mM IBMX (3-isobytyl-1-methyl xanthine), 0.5 μM dexamethasone and 5 μg/ml insulin (MDI) for 2 days, and further cultured in 10% FBS/high-glucose DMEM containing only 5 μg/ml insulin(I) for 4 days, followed by again culturing in 10% FBS/high-glucose DMEM for another 6 days. Thus, the cells were cultured for a total of 10 days to differentiate into adipocytes. After confluent culture, the cells were treated with the compounds at a concentration of 10 μM each time the medium was changed. On day 10 after differentiation, the cultured cells were fixed with 4% paraformaldehyde and then lipid droplets were stained using BODIPY, a marker of lipid droplets, and the nuclei in cells were labeled through DAPI staining. The results are illustrated in FIG. 3.

In FIG. 3, a green circular structure represents a lipid droplet accumulated in cells, which shows that the size and number of lipid droplets were reduced by the treatment of the compounds according to the present invention. Therefore, it was confirmed that the compound of the present invention is effective for removing lipid droplets in preadipocytes.

Experimental Example 4: Analysis of the Effect of Decomposing Lipid Droplets in 3T3-L1 and Hep G2 Cells Via Lipophagy by the Compound of the Present Invention The following experiment was conducted to confirm that the lipid droplets are decomposed via lipophagy by the compound of the present invention.

3T3-L1 preadipocytes were purchased from Korean Cell Line Bank, and cultured and maintained in newborn calf serum (NCS, Invitrogen Corporation, Auckland, New Zealand) and high-glucose DMEM (high glucose Dulbecco's modified Eagle's Medium, Sigma Co., St. Louis, Mo., USA). For adipocyte differentiation, 3T3-L1 with a concentration of 100,000 cells/ml were grown to confluence with 10% fetal bovine serum (FBS) and high glucose DMEM for 2 days, then cultured in 10% FBS/high-glucose DMEM containing 0.5 mM IBMX (3-isobytyl-1-methyl xanthine), 0.5 µM dexamethasone and 5 µg/ml insulin (MDI) for 2 days, and further cultured in 10% FBS/high-glucose DMEM containing only 5 µg/ml insulin(I) for 4 days, followed by again culturing in 10% FBS/high-glucose DMEM alone for another 6 days. Thus, the cells were cultured for a total of 10 days to differentiate into adipocytes. After confluent culture, the cells were treated with the compounds at a concentration of 10 µM each time the medium was changed.

In addition, Hep G2 hepatocytes were inoculated into a 24 well cell culture plate containing a cover slip, cultured in a DMEM medium containing 1 mM of oleic acid and 0.5 mM of palmitic acid for 24 hours to induce lipid accumulation, which was then treated with 10 µM of each compound and incubated for another 24 hours.

Subsequently, each cell was then washed twice with PBS solution, fixed with 4% paraformaldehyde solution for 15 minutes, and blocked in PBS solution containing 2% BSA for 1 hour. After blocking was completed, it was subjected to a primary antibody reaction. The primary antibody reaction was performed using LC3 rabbit polyclonal antibody (1:300, Sigma-Aldrich, USA) overnight at 4° C. After completion of the primary antibody reaction, cover slips were washed twice with PBS, and a secondary antibody (1:500, goat anti rabbit Alexa flour 555, Thermo Fisher, US) was reacted at room temperature for 1 hour. After completion of the secondary antibody reaction, the cells were washed twice with PBS, and then BODIPY 493/503 was reacted at room temperature for 10 minutes and mounted on a slide glass using a mounting medium. The stained cells were photographed using a confocal microscope, and the results are illustrated in FIG. 4.

In FIG. 4a, a green circular structure represents a lipid droplet accumulated in cells, and it can be confirmed that the lipid droplets were accumulated in 3T3-L1 preadipocytes during the differentiation process into the adipocytes. When treating the compounds of the present invention with the completion of differentiation into adipocytes, it can be confirmed that red stained LC3, which is a marker capable of tracking the level of lipophagy activity, was increased as compared with cell treated with placebo. In addition, comparing the degree of overlap between lipid droplets and LC3, it can be confirmed that when treated with the compounds of the present invention, the degree of overlap was significantly increased as compared with cells treated with placebo. Therefore, it could be seen that the size and number of the lipid droplets produced in the 3T3-L1 adipocytes were reduced due to the action of lipophagy increased by the compound of the present invention.

Further, in FIG. 4b, the green circular structures represent lipid droplets accumulated in cells, and it can be confirmed that by treating oleic acid and palmitic acid, which are one type of fatty acids, the accumulation of lipid droplets was induced as compared with the control group treated with BSA. When treated with the compounds according to the present invention after treatment with oleic acid and palmitic acid, it can be confirmed that the red-stained LC3, which is a marker capable of tracking the level of the lipophagy activity, was increased. It is also shown that LC3, a marker of lipophagy, is located on the surface of lipid droplets through images obtained by superimposing an image of green-stained lipid droplets and an image of red-stained LC3. Thus, it could be seen that the effect of reducing the number and size of lipid droplets exhibited by the compounds of the present invention was mediated by the action of lipophagy.

In addition, in order to confirm that removal of lipid droplets by the treatment of the compound according to the present invention resulted from the action of lipophagy, Bifilomycin, an inhibitor of the action of lipophagy, and 5 nM of the compound of the present invention were treated together to adipocytes differentiated from pre-adipocytes to accumulate lipid droplets, but it was confirmed that the removal effect of lipid droplets was not exhibited. The results are illustrated in FIG. 5.

In FIG. 5, the red circular structures represent lipid droplets, which show that the lipid droplets reduced by the compounds of the present invention did not decrease in response to the treatment of bafilomycin. Thus, in view of the fact that the reduction effect of the number and size of lipid droplets did not appear when treated with the compound according to the present invention, it could be seen that the effect of removing lipid droplets by the present compound was caused by the action of lipophagy.

Experimental Example 5: Analysis of the Weight Loss Effect of the Compound of the Present Invention in High-Fat Diet-Fed Mice In order to induce obesity in experimental mice, wild-type C57BL6 mice (6 weeks old) were supplied from Medical Center for Experimental Animal Resource Development, Seoul National University and divided into general feed intake group (LFD) and high calorie diet intake group (HFD) through random assignment. The high-fat intake group was again divided into a group treated with placebo and a group treated with the compound of the present invention, and divided into a total of three groups to conduct obesity induction and compound treatment at the same time. As a result, it was analyzed whether the compound could effectively remove the fat inflowing excessively and thus prevent obesity.

Specifically, the mice that had been supplied were allowed to freely consume water after a week of adaptation period in the rearing cage. As for diets, high-fat diets (protein: 10%, carbohydrate: 30%) in which 60% of the total calories (4.60 kcal/g) is composed of fat, and normal diets (protein: 18.8%, carbohydrate: 63.9%) in which 17.2% of the total calories (3.8 kcal/g) was composed of fat, were supplied, respectively. In order to evaluate the preventive and therapeutic effects of obesity, etc., the compound of the present invention was dissolved in DMSO at 1 µL/mg (v/w), then diluted with PBS, and administered intraperitoneally three times per week at a concentration of 20 µg/g body weight of mice. In the placebo-treated group, the same amount of DMSO was diluted with PBS and administered. In order to evaluate the weight gain associated with the high-fat diet intake and the weight loss suppressing effect associated with the administration of the compound of the present invention, mice body weights were measured three times a week. In order to verify the removal effect of the body fat in mice, euthanasia was induced by excessive supply of $CO_2$ after 24 hours including an 8 hour fasting period after the final administration, and then laparotomy was performed, and changes in body fat were observed. The results of the body fat removing effect, the change in body weight, the difference in feed intake and the difference in height due to the administration of the high fat diets and the compound according to the present invention are illustrated in FIGS. 6, 7, 8, 9, 10 and 11, respectively.

As illustrated in FIG. 6, when the compound of the present invention was administered, it can be confirmed that the size of the accumulated abdominal fat was significantly reduced as compared with the placebo-treated group. A significant reduction in body fat eventually resulted in weight loss, and the results are illustrated in FIG. 7.

In light of the fact that a significant difference in feed intake was not exhibited, it can be confirmed from FIGS. 8 to 10 that the weight loss due to the weight reduction of white adipose tissue is not a phenomenon due to a decrease in inflow of fat into the body, but the disappearance of the white adipose tissue directly occurs in the body. The results showed that only the weight of the adipose tissue was reduced, without being affected by other tissues.

Further, the percentage of weight loss, change in height, and change in feed intake through the compounds according to the present invention are illustrated in FIG. 11. These results are derived from the investigation results of the feed intake in order to determine whether the weight loss effect is due to the decrease of the feed intake, indicating that no significant differences were exhibited.

Further, in order to understand that the weight loss caused by the compounds of the present invention has an effect on blood lipid components, blood glucose and pathological conditions of tissues, the results of the items that have examined blood samples taken from the placebo-treated mice and the compound-administered mice are illustrated in FIG. 12. As a result, it was confirmed that triglyceride levels in the blood were significantly reduced.

Experimental Example 6: Analysis of the Effect of the Compound of the Present Invention on the Removal of Lipid Droplets in Tissues of High-Fat Diets-Fed Mice Using HnE Staining Method In order to confirm the removal effect of lipid droplets accumulated in tissues by the compound of the present invention, the hepatic tissues of the mice of the previous Experimental Example 5 were observed through HnE staining method, and the results are illustrated in FIG. 13. In FIG. 13, the white circular structures indicated by yellow arrows represent lipid droplets, from which it can be seen that the size and number of lipid droplets accumulated in hepatocytes were decreased by the treatment of the compound of the present invention.

To confirm that the size of adipocytes was reduced by the compounds of the present invention, the adipose tissue of the mouse of the previous Experimental Example 5 was observed through the HnE staining method, and the results are illustrated in FIG. 14. In FIG. 14, the structures indicated by blue arrows and black and yellow dots represent adipocytes in adipose tissue, from which it can be seen that the size of the adipocytes was reduced by the treatment of the compounds.

Experimental Example 7: Analysis of the Effect of Removing Lipid Droplets by the Action of Lipophagy Using Immunohistochemical Staining Method The mice of the previous Experimental Example 5 were dissected to analyze whether reduction or removal of lipid droplets in liver has occurred through immunohistochemical staining method. The staining solution used for immunohistochemical staining was purchased from Sigma-Aldrich. All procedures were performed on 5-μm sections of liver tissue embedded in paraffin at room temperature. Antigen regeneration was performed on formalin fixed tissue for 15 minutes at 100° C. in a water bath prior to immunohistochemical staining. Endogenous peroxidase activity was blocked by hydrogen peroxide. Primary antibodies were detected with HRP-conjugated polymer and developed by DAB. Slides were then counterstained with hematoxylin, and subjected to multi-stage alcohol dehydration and mounted with a mounting medium. The results are illustrated in FIG. 15. In FIG. 15, it can be seen that LC3 protein stained in brown color on the surface of the lipid droplets was disposed in the area indicated by the yellow square. From this, it can be seen that the removal of lipid droplets was directly caused by the action of lipophagy occurring on the surface of the lipid droplets.

In addition, in order to observe the relaxation effect of the compound of the present invention in inflammatory symptoms in hepatic tissues caused by the excessive accumulation of lipid droplets, the expression pattern of macrophages, which are inflammatory cells, was observed through tissue immunochemical staining method, The results are illustrated in FIG. 16. In FIG. 16, the brown-labeled cells represent macrophages, from which it could be seen that macrophages accumulated in hepatic tissues were decreased by the treatment of the compound of the present invention. Thereby, it can be seen that macrophages accumulated in hepatic tissues were decreased by the treatment of the compound of the present invention.

The invention claimed is:

1. A compound represented by the following Chemical Formula 1 or a pharmaceutically acceptable salt thereof,

[Chemical Formula 1]

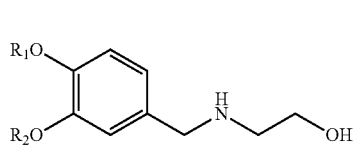

in Chemical Formula 1,
$R_1$ is -$L_1$-(phenyl),
$R_2$ is hydrogen, or -$L_2$-(phenyl),
$L_1$ is $C_{1-5}$ alkylene, and
$L_2$ is $C_{1-5}$ alkylene,
with the proviso that not both $R_1$ and $R_2$ are benzyl.

2. The compound or a pharmaceutically acceptable salt thereof according to claim 1, wherein
$L_1$ is —$CH_2$—, —$CH_2CH_2$—, —$CH_2CH_2CH_2$—, or —$CH_2CH_2CH_2CH_2$—.

3. The compound or a pharmaceutically acceptable salt thereof according to claim 1, wherein
$L_2$ is —$CH_2$—, —$CH_2CH_2$—, —$CH_2CH_2CH_2$—, or —$CH_2CH_2CH_2CH_2$—.

4. The compound or a pharmaceutically acceptable salt thereof according to claim 1, wherein
$R_1$ is —$CH_2$-(phenyl), and
$R_2$ is hydrogen, —$CH_2CH_2$-(phenyl), —$CH_2CH_2CH_2$-(phenyl), or —$CH_2CH_2CH_2CH_2$-(phenyl).

5. The compound or a pharmaceutically acceptable salt thereof according to claim 1, wherein
$R_1$ and $R_2$ are equal to each other.

6. The compound or a pharmaceutically acceptable salt thereof according to claim 5, wherein R₁ and R₂ are —CH₂CH₂-(phenyl), —CH₂CH₂CH₂-(phenyl), or —CH₂CH₂CH₂CH₂-(phenyl).

7. The compound or a pharmaceutically acceptable salt thereof according to claim 1, wherein
the compound is any one selected from the group consisting of:
1) 2-(3,4-diphenethoxybenzylamino)ethanol,
2) 2-(3,4-bis(3-phenylpropoxy)benzylamino)ethanol,
3) 2-(3,4-bis(4-phenylbutoxy)benzylamino)ethanol,
4) 2-(benzyloxy)-5-((2-hydroxyethylamino)methyl)phenol,
5) 2-(4-(benzyloxy)-3-phenethoxybenzylamino)ethanol,
6) 2-(4-(benzyloxy)-3-(3-phenylpropoxy)benzylamino)ethanol, and
7) 2-(4-(benzyloxy)-3-(4-phenylbutoxy)benzylamino)ethanol.

8. A method for preventing or treating obesity or metabolic syndrome in a subject in need thereof, comprising administering to the subject the compound or a pharmaceutically acceptable salt thereof according to claim 1.

9. The method according to claim 8, wherein the metabolic syndrome is any one selected from the group consisting of myocardial infarction, arteriosclerosis, hyperlipidemia, hypertension, cerebral infarction, cerebral hemorrhage, fatty liver, and type 2 diabetes mellitus.

* * * * *